US007378404B2

(12) United States Patent
Peters et al.

(10) Patent No.: US 7,378,404 B2
(45) Date of Patent: *May 27, 2008

(54) 8β-HYDROCARBYL-SUBSTITUTED ESTRATRIENES FOR USE AS SELECTIVE ESTROGENS

(75) Inventors: Olaf Peters, Jena (DE); Alexander Hillisch, Jena (DE); Ina Thieme, Graitschen (DE); Walter Elger, Berlin (DE); Christa Hegele-Hartung, Muelheim a. d Ruhr (DE); Uwe Kollenkirchen, Berlin (DE); Karl-Heinrich Fritzemeier, Berlin (DE); Vladimir Patchev, Jena (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/257,288

(22) PCT Filed: Apr. 12, 2001

(86) PCT No.: PCT/EP01/04290

§ 371 (c)(1),
(2), (4) Date: Apr. 1, 2003

(87) PCT Pub. No.: WO01/77139

PCT Pub. Date: Oct. 18, 2001

(65) Prior Publication Data

US 2003/0176405 A1 Sep. 18, 2003

Related U.S. Application Data

(60) Provisional application No. 60/207,370, filed on May 26, 2000.

(30) Foreign Application Priority Data

Apr. 12, 2000 (DE) ................................ 100 19 167

(51) Int. Cl.
*A61K 31/56* (2006.01)
*C07J 1/00* (2006.01)

(52) U.S. Cl. ...................... 514/179; 514/182; 552/617; 552/625; 552/626

(58) Field of Classification Search ................ 552/617, 552/625, 626; 514/179, 182
See application file for complete search history.

(56) References Cited

U.S. PATENT DOCUMENTS 3,681,407 A    8/1972  Los
3,736,345 A *  5/1973  Los ............................. 260/465
3,806,546 A *  4/1974  Los ............................. 260/566
4,961,931 A   10/1990  Wong

FOREIGN PATENT DOCUMENTS

| DE | 4018828  | * 12/1990 |
| FR | M2743    | *  9/1964 |
| JP | 45004059 | *  2/1970 |
| JP | 45004060 |    2/1970 |
| JP | 45004061 |    2/1970 |
| JP | 45024572 |    8/1970 |

OTHER PUBLICATIONS

Database Chemabs 'Online!, Chemical Abstracts Service, Columbus, Ohio, US; Nagata, Wataru et al., "8. Beta. -Cyanoestanes derivatives," retrieved from STN, Database accession No. 73:109984, XP002175034, abstract.

Database Chemabs 'Online!, Chemical Abstracts Service, Columbus, Ohio, US; Nagata, Wataru et al: "8.beta.-Methylestradiols," retrieved from STN, Database accession No. 73:25750, XP002175035, abstract.

Database Chemabs 'Online!, Chemical Abstracts Service, Columbus, Ohio, US; Nagata, Wataru et al., "8.beta.-Methylestranes," retrieved from STN, Database accession No. 73:25749, XP002175036, abstract.

Database Chemabs 'Online!, Chemical Abstracts Service, Columbus, Ohio, US; Nagata, Wataru et. al., "8.beta.-Methyl-9-dehydroestrone 3-ethers," retrieved from STN, Database accession No. 73:25748, XP002175037, abstract.

Elger et al., "Novel oestrogen sulfamates: a new approach to oral hormone therapy," Expert Opinion on Investigational Drugs, Apr. 1998, pp. 575-589, vol. 7, No. 4, XP002121926, ISSN: 1354-3784; p. 580-p. 581; tables 2-5, Ashley Publications Ltd., London, GB.

(Continued)

*Primary Examiner*—Barbara P. Badio
(74) *Attorney, Agent, or Firm*—Millen, White, Zelano & Branigan, P.C.

(57) ABSTRACT

This invention describes the new 8β-substituted estratrienes of general formula I in which $R^2$, $R^3$, $R^6$, $R^{6'}$, $R^7$, $R^{7'}$, $R^9$, $R^{11}$, $R^{11'}$, $R^{12}$, $R^{14}$, $R^{15}$, $R^{15'}$, $R^{16}$, $R^{16'}$, $R^{17}$ and $R^{17'}$ have the meanings that are indicated in the description, and $R^8$ means a straight-chain or branched-chain, optionally partially or completely halogenated alkyl or alkenyl radical with up to 5 carbon atoms, an ethinyl- or prop-1-inyl radical, as pharmaceutical active ingredients that have in vitro a higher affinity to estrogen receptor preparations of rat prostates than to estrogen receptor preparations of rat uteri and in vivo preferably a preferential action on bone rather than the uterus and/or a pronounced action with respect to stimulation of the expression of 5HT2a-receptors and 5HT2a-transporters, their production, their therapeutic use and pharmaceutical dispensing forms that contain the new compounds. The invention also describes the use of these compounds for treatment of estrogen-deficiency-induced diseases and conditions as well as the use of an 8β-substituted estratriene structural part in the total structures of compounds that have a dissociation in favor of their estrogenic action on bones rather than the uterus.

41 Claims, 3 Drawing Sheets

OTHER PUBLICATIONS

Fevig T L et al., "Estrogen receptor binding tolerance of 16-alpha-substituted estradiol derivatives," Steroids: Structure, Function, and Regulation, 1988, pp. 471-498, vol. 51, No. 5-6, XP002159339, ISSN: 0039-128X; p. 485; example 3; table 1, Elsevier Science Publishers, New York, NY, US.

Database Biosis 'Online!, Biosciences Information Service, Philadelphia, PA, US; Fernandez A I et al., "Influence of hormonal status in relaxant effect of diethylstilbestrol and nifedipine on isolated rat uterus contraction," 1995, Database accession No. PREV199598457779, XP002175038, abstract; & General Pharmacology, 1995, pp. 1281-1287, vol. 26, No. 6, ISSN: 0306-3623, abstract only.

* cited by examiner

Figure 1: Description of the synthesis of 1 in: R. P. Stein, G. C. Buxby, R. C. Smith and H. Smith, "11-Oxygenated Steroids and Process for Their Preparation," US 3491089, Patented 1/20/1970.

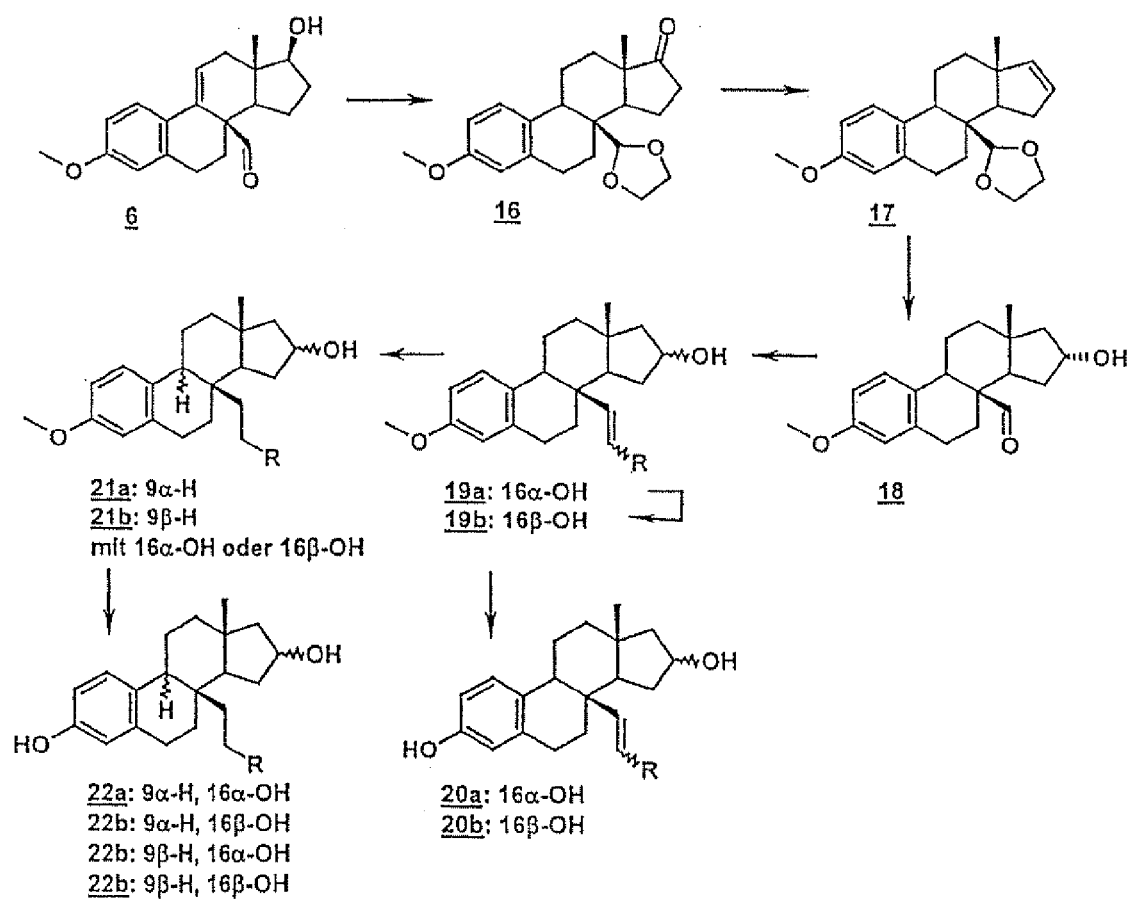
Figure 3: [Key:] mit 16α-OH oder 16β-OH = with 16α-OH or 16β-OH

8β-HYDROCARBYL-SUBSTITUTED ESTRATRIENES FOR USE AS SELECTIVE ESTROGENS

This application is a 371 of PCT/EP01/04290, filed Apr. 12, 2001, which claims the benefit of U.S. Provisional Application Ser. No. 60/207,370, filed on May 26, 2000.

FIELD OF THE INVENTION

This invention relates to new compounds as pharmaceutical active ingredients, which have in vitro a higher affinity to estrogen receptor preparations from rat prostates than to estrogen receptor preparations from rat uteri and in vivo a preferential action on bone rather than the uterus and/or a pronounced action with respect to stimulation of the expression of 5HT2a-receptors and 5HT2a-transporters, their production, their therapeutic use and pharmaceutical dispensing forms that contain the new compounds. The chemical compounds are novel, steroidal, tissue-selective estrogens.

BACKGROUND OF THE INVENTION

Established estrogen therapies for treatment of hormone-deficiency-induced symptoms and the protective action of estrogens on bones, brains, vessels and other organ systems.

The efficiency of estrogens in the treatment of hormone-deficiency-induced symptoms such as hot flashes, atrophy of estrogen target organs and incontinence, as well as the successful use of estrogen therapies for prevention of bone mass loss in peri- and postmenopausal women, is well documented and generally accepted (Grady et al. 1992, Ann Intern Med 117: 1016-1037). It is also well documented that estrogen replacement therapy in postmenopausal women or in women with ovarian dysfunction that is caused in some other way reduces the risk of cardiovascular diseases compared to non-estrogen-treated women (Grady et al., loc. cit.).

In addition, more recent studies confirm a protective action of estrogens against neurodegenerative diseases, such as, e.g., Alzheimer's disease (Henderson 1997, Neurology 48 (Suppl 7): pp. 27-35; Birge 1997, Neurology 48 (Suppl 7): pp.36-41), a protective action with respect to brain functions, such as memory and learning capacity (McEwen et al. 1997, Neurology 48 (Suppl 7): pp. 8-15; Sherwin 1997, Neurology 48 (Suppl 7): pp. 21-26), as well as against hormone-deficiency-induced mood swings (Halbreich 1997, Neurology 48 (Suppl 7): pp. 16-20).

In addition, estrogen replacement therapy has proven effective relative to the reduction of the incidence of colorectal carcinoma (Calle, E. F. et al., 1995, J Natl Cancer Inst 87: 517-523).

In conventional estrogen or hormone replacement therapy (=HRT), natural estrogens, such as estradiol, and conjugated estrogens that consist of equine urine are used either by themselves or in combination with a gestagen. Instead of the natural estrogens, derivatives that are obtained by esterification, such as, e.g., 17β-estradiol-valerate, can also be used.

Because of the stimulating action of the estrogens that are used on the endometrium, which results in an increase of the risk of endometrial carcinoma (Harlap, S. 1992, Am J Obstet Gynecol 166: 1986-1992), estrogen/gestagen combination preparations are preferably used in hormone replacement therapy. The gestagenic component in the estrogen/gestagen combination avoids hypertrophy of the endometrium, but the occurrence of undesirable intracyclic menstrual bleeding is also linked to the gestagen-containing combination.

Selective estrogens represent a more recent alternative to the estrogen/gestagen combination preparations. Up until now, selective estrogens have been defined as those compounds that have an estrogen-like effect on the brain, bones and vascular system, owing to their antiuterotrophic (i.e., antiestrogenic) partial action, but they do not have a proliferative effect on the endometrium.

A class of substances that partially meet the desired profile of a selective estrogen are the so-called "Selective Estrogen Receptor Modulators" (SERM) (R. F. Kauffman, H. U. Bryant 1995, DNAP 8 (9): 531-539). In this case, these are partial agonists of estrogen receptor subtype "ERα." This substance type is ineffective, however, with respect to the therapy of acute postmenopausal symptoms, such as, e.g., hot flashes. As an example of a SERM, the raloxifene that was recently introduced for the indication of osteoporosis can be mentioned.

Estrogen Receptor Beta (ERβ)

Estrogen receptor β (ERβ) was recently discovered as a second subtype of the estrogen receptor (Kuiper et al. (1996), Proc. Natl. Acad. Sci. 93: 5925-5930; Mosselman, Dijkema (1996) Febs Letters 392: 49-53; Tremblay et al. (1997), Molecular Endocrinology 11: 353-365). The expression pattern of ERβ differs from that of the ERα (Kuiper et al. (1996), Endocrinology 138: 863-870). ERβ thus predominates over ERα in the rat prostate, while ERα predominates over ERβ in the rat uterus. Areas in which in each case only one of the two ER-subtypes is expressed were identified in the brain (Shugrue et al. (1996), Steroids 61: 678-681; Li et al. (1997), Neuroendocrinology 66:63-67). ERβ is expressed in, i.a., areas that are considered to be important for cognitive processes and "mood" (Shugrue et al. 1997, J Comparative Neurology 388: 507-525).

Molecular targets for ERβ in these brain areas could be the 5HT2a-receptor and the serotonin transporter (G. Fink & B. E. H. Sumner 1996 Nature 383:306; B. E. H. Sumner et al. 1999 Molecular Brain Research, in press). The neurotransmitter serotonin (5-hydroxytryptamine) is involved in the regulation of a considerable number of processes, which can be impaired in menopause. In particular, the effects of menopause on emotion and cognition are connected with the serotoninergic system. Estrogen replacement therapy has proven effective with respect to treatment of these estrogen deficiency-produced symptoms, possibly by modulation of serotonin receptor and transporter expression.

Other organ systems with comparatively higher ERβ-expression encompass the bones (Onoe, Y. et al., 1997, Endocrinology 138: 4509-4512), the vascular system (Register, T. C., Adams, M. R. 1998, J. Steroid Molec Biol 64: 187-191), the urogenital tract (Kuiper, G. J. M. et al. 1997, Endocrinology 138: 863-870), the gastrointestinal tract (Campbell-Thopson 1997, BBRC 240: 478-483), as well as the testis (Mosselmann, S. et al. 1996 Febs Lett 392 49-53) including the spermatides (Shugrue et al. 1998, Steroids 63: 498-504). The tissue distribution suggests that estrogens regulate organ functions via ERβ. The fact that ERβ is functional in this respect also follows by studies in ERα-(ERKO) or ERβ-(βERKO)-knockout mice: ovariectomy produces bone mass loss in ERKO-mice, which can be cancelled out by estrogen substitution (Kimbro et al. 1998, Abstract OR7-4, Endocrine Society Meeting New Orleans). Estradiol in the blood vessels of female ERKO mice also inhibits vascular media and smooth muscle cell proliferation (Iafrati, M. D. et al. 1997, Nature Medicine 3: 545-548). These protective actions of estradiol are carried out in the ERKO mouse presumably via ERβ.

Observations of βERKO mice provide an indication on a function of ERβ in the prostate and bladder: in the case of older male mice, symptoms of prostate and bladder hyperplasia occur (Krege, J. H. et al. 1998, Proc Natl Acad Sci 95: 15677-15682). In addition, female ERKO mice (Lubahn, D. B. et al. 1993, Proc Natl Acad Sci 90: 11162-11166) and male ERKO mice (Hess, R. A. et al. 1997, Nature 390: 509-512) as well as female βERKO mice (Krege, J. H., 1998) have fertility disorders. Consequently, the important function of estrogens with respect to maintaining testis and ovary functions as well as fertility is confirmed.

It was possible to achieve a selective estrogen action on specific target organs by subtype-specific ligands based on the different tissue or organ distribution of the two subtypes of the ERs. Substances with a preference for ERβ compared to ERα in the in vitro receptor binding test were described by Kuiper et al. (Kuiper et al. (1996), Endocrinology 138: 863-870). A selective action of subtype-specific ligands of the estrogen receptor on estrogen-sensitive parameters in vivo was not previously shown.

The object of this invention is therefore to prepare compounds that have in vitro a dissociation with respect to the binding to estrogen receptor preparations from rat prostates and rat uteri and that have in vivo a dissociation with respect to bones rather than the uterus action. The compounds are to have in vitro a higher affinity to estrogen receptor preparations from rat prostates than to estrogen receptor preparations from rat uteri and in vivo a higher potency with respect to protection against hormone-deficiency-induced bone mass loss in comparison to uterus-stimulating action in the uterus and/or pronounced action with respect to stimulation of the expression of 5HT2a-receptors and 5HT2a-transporters.

In the broader sense, a structure-action relationship, which allows for access to compounds that have the above-formulated pharmacological profile of better estrogenic action on bones than on the uterus, is to be made available by this invention.

According to the invention, the object above is achieved by the provision of 8β-substituted estra-1,3,5(10)-triene derivatives of general formula I'

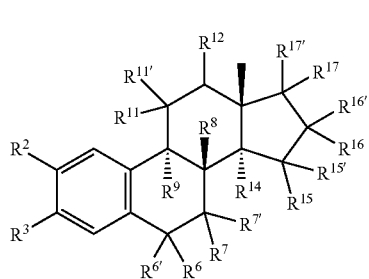

(I')

in which
R$^2$ means a hydrogen atom, a halogen atom;
a radical R$^{18}$— or R$^{18}$—O—, whereby R$^{18}$ means a hydrogen atom or a straight-chain or branched-chain, saturated or unsaturated hydrocarbon radical with up to 6 carbon atoms, a trifluoromethyl group;
a group R$^{19}$SO$_2$—O—, in which R$^{19}$ is an R$^{20}$R$^{21}$N group, whereby R$^{20}$ and R$^{21}$, independently of one another, mean a hydrogen atom, a C$_1$-C$_5$-alkyl radical, a group C(O)R$^{22}$, in which R$^{22}$ represents an optionally substituted, straight-chain or branched-chain, saturated or unsaturated in up to three places, optionally partially or completely halogenated hydrocarbon radical with up to 10 carbon atoms, an optionally substituted C$_3$-C$_7$-cycloalkyl radical, an optionally substituted C$_4$-C$_{15}$-cycloalkylalkyl radical or an optionally substituted aryl, heteroaryl or aralkyl radical, or, together with the N-atom, means a polymethylenimino radical with 4 to 6 C atoms or a morpholino radical;

R$^3$ means a group R$^{18}$—O—, R$^{19}$SO$_2$—O— or —O—C(O)R$^{22}$, with R$^{18}$, R$^{19}$ and R$^{22}$ in each case in the meaning that is indicated under R$^2$, whereby in addition an aryl, heteroaryl or aralkyl radical can stand for R$^{18}$;

R$^6$ and R$^7$ each mean a hydrogen atom or together an additional bond;

R$^{6'}$ and R$^{7'}$, independently of one another, mean a hydrogen atom, a halogen atom, a group R$^{18}$—O—, R$^{19}$SO$_2$—O— or —R$^{22}$, with R$^{18}$, R$^{19}$ and R$^{22}$ in each case in the meaning that is indicated under R$^2$;

R$^8$ means a straight-chain or branched-chain, optionally partially or completely halogenated alkyl or alkenyl radical with up to 5 carbon atoms, an ethinyl or prop-1-inyl radical;

R$^9$ means a hydrogen atom, a straight-chain or branched-chain, saturated or unsaturated hydrocarbon radical with up to 5 carbon atoms, or together with R$^{11}$ means an additional bond;

R$^{11}$ means a hydrogen atom or together with R$^9$ or together with R$^{12}$ means an additional bond;

R$^{11'}$ means a hydrogen atom, a halogen atom, a saturated or unsaturated, optionally partially or completely halogenated (F, Cl) hydrocarbon radical, which has a maximum linear chain length of 4 carbon atoms, or a group —X—R$^{18'}$, in which X is an oxygen or sulfur atom, and R$^{18'}$is an alkyl radical with 1 to 3 carbon atoms;

R$^{12}$ means a hydrogen atom or together with R$^{11}$ means an additional bond;

R$^{14}$ means a hydrogen atom or together with R$^{15}$ means an additional bond;

R$^{15}$ means a hydrogen atom or together with R$^{14}$ or together with R$^{16}$ means an additional bond;

R$^{16}$ means a hydrogen atom or together with R$^{15}$ means an additional bond;

R$^{15'}$ and R$^{16'}$, independently of one another, mean a hydrogen atom, a halogen atom, a group R$^{18}$—O—, R$^{19}$SO$_2$—O— or —R$^{22}$, with R$^{18}$, R$^{19}$ and R$^{22}$ in each case in the meaning that is indicated under R$^2$;

R$^{17}$ and R$^{17'}$ each mean a hydrogen atom; a hydrogen atom and a halogen atom; a hydrogen atom and a benzyloxy group; a hydrogen atom and a group R$^{19}$SO$_2$—O—;
a group R$^{18}$ and a group —C(O)R$^{22}$ or —O—C(O)R$^{22}$; a group R$^{18}$—O— and a group R$^{18}$—; a group R$^{18}$—O— and a group —O—C(O)R$^{22}$, in all above cases with R$^{18}$, R$^{19}$ and R$^{22}$ in each case in the meaning that is indicated under R$^2$; or R$^{17}$ and R$^{17'}$ together mean a group =CR$^{23}$R$^{24}$, in which R$^{23}$ and R$^{24}$, independently of one another, represent a hydrogen atom and a halogen atom, or together an oxygen atom;

for treatment of estrogen-deficiency-induced diseases and conditions.

The possible substituents at carbon atoms 6, 7, 9, 11, 15, 16 and 17 can be respectively in α- or β-position.

According to a variant of the invention, preferably compounds of general formula I' are used, in which
- $R^2$ means a hydrogen or halogen atom or a hydroxy group;
- $R^3$ means a group $R^{18}$—O—, $R^{19}SO_2$—O— or —O—C(O)$R^{22}$, with $R^{18}$, $R^{19}$ and $R^{22}$ in each case in the meaning that is indicated under $R^2$, whereby in addition an aryl or aralkyl radical can stand for $R^{18}$;
- $R^6$ and $R^7$ each mean a hydrogen atom;
- $R^{6'}$ means a hydrogen atom, a hydroxy group, a group $R^{22}$ in the meaning that is indicated under $R^2$;
- $R^{7'}$ means a hydrogen atom, a halogen atom, a group $R^{18}$—O—, $R^{19}SO_2$—O— or —$R^{22}$, with $R^{18}$, $R^{19}$ and $R^{22}$ in each case in the meaning that is indicated under $R^2$;
- $R^8$ means a straight-chain or branched-chain, optionally partially or completely halogenated alkyl or alkenyl radical with up to 5 carbon atoms, an ethinyl- or prop-1-inyl radical;
- $R^9$ means a hydrogen atom or together with $R^{11}$ an additional bond;
- $R^{11}$ means a hydrogen atom or together with $R^9$ an additional bond;
- $R^{11'}$ means a hydrogen atom, a halogen atom, a saturated or unsaturated, optionally partially or completely halogenated (F, Cl) hydrocarbon radical, which has a maximum linear chain length of 4 carbon atoms, or a group —X—$R^{18'}$, in which X is a sulfur atom, and $R^{18'}$, is an alkyl radical with 1 to 3 carbon atoms;
- $R^{12}$, $R^{14}$, $R^{15}$ and $R^{16}$ in each case mean a hydrogen atom;
- $R^{16'}$ means a hydrogen atom, a halogen atom, a group $R^{18}$—O—, $R^{19}SO_2$—O— or —$R^{22}$, with $R^{18}$, $R^{19}$, and $R^{22}$ in each case in the meaning that is indicated under $R^2$;
- $R^{17}$ and $R^{17'}$ in each case mean a hydrogen atom; a hydrogen atom and a halogen atom; a hydrogen atom and a benzyloxy group; a hydrogen atom and a group $R^{19}SO_2$—O—;
  - a group $R^{18}$ and a group —C(O)$R^{22}$ or —O—C(O)$R^{22}$; a group $R^{18}$—O— and a group $R^{18}$—; a group $R^{18}$—O— and a group —O—C(O)$R^{22}$, in all above cases with $R^{18}$, $R^{19}$ and $R^{22}$ in each case in the meaning that is indicated under $R^2$; and
- $R^{17}$ and $R^{17'}$ together mean a group =$CR^{23}R^{24}$, in which $R^{23}$ and $R^{24}$, independently of one another, represent a hydrogen atom and a halogen atom, or together an oxygen atom.

Another preferred variant of this invention calls for the use of those compounds of general formula I', in which
- $R^2$ means a hydrogen atom or a fluorine atom or a hydroxy group,
- $R^3$ means a group $R^{18}$—O—, $R^{19}SO_2$—O— or —O—C(O)$R^{22}$, with $R^{18}$, $R^{19}$, and $R^{22}$ in each case in the meaning that is indicated under $R^2$, whereby in addition an aryl or aralkyl radical can stand for $R^{18}$;
- $R^6$ and $R^7$ in each case mean a hydrogen atom;
- $R^{6'}$ means a hydrogen atom or a hydroxy group,
- $R^{7'}$ means a hydrogen atom, a fluorine or chlorine atom, a group $R^{18}$—O—, $R^{19}SO_2$—O— or —$R^{22}$, with $R^{18}$, $R^{19}$ and $R^{22}$ in each case in the meaning that is indicated under $R^2$;
- $R^8$ means a straight-chain or branched-chain, optionally partially or completely fluorinated alkyl or alkenyl radical with up to 5 carbon atoms, an ethinyl radical or prop-1-inyl radical;
- $R^9$, independently of one another, mean a hydrogen atom or together with $R^{11}$ an additional bond;
- $R^{11'}$ means a hydrogen atom, a fluorine or chlorine atom, a saturated, straight-chain or branched-chain $C_1$-$C_4$-alkyl group, a group —X—$R^{18'}$, in which X is a sulfur atom and $R^{18'}$ means a saturated, straight-chain or branched-chain $C_1$-$C_3$-alkyl group, a chloromethyl or chloroethyl group;
- $R^{12}$, $R^{14}$, $R^{15}$ and $R^{16}$ in each case mean a hydrogen atom;
- $R^{16'}$ means a hydrogen atom, a fluorine or chlorine atom or a group $R^{18}$—O— or —$R^{22}$, with $R^{18}$ and $R^{22}$ in each case in the meaning that is indicated under $R^2$;
- $R^{17}$ and $R^{17'}$ in each case mean a hydrogen atom; a hydrogen atom and a halogen atom; a hydrogen atom and a benzyloxy group; a hydrogen atom and a group $R^{19}SO_2$—O—;
  - a group $R^{18}$ and a group —C(O)$R^{22}$ or —O—C(O)$R^{22}$; a group $R^{18}$—O— and a group $R^{18}$—; a group $R^{18}$—O— and a group —O—C(O)$R^{22}$, in all above cases with $R^{18}$, $R^{19}$ and $R^{22}$ in each case in the meaning that is indicated under $R^2$; or
- $R^{17}$ and $R^{17'}$ together mean a group =$CR^{23}R^{24}$, in which $R^{23}$ and $R^{24}$, independently of one another, represent a hydrogen atom and a halogen atom, or together an oxygen atom.

According to another variant, 8β-substituted estra-1,3,5 (10)-triene derivatives of general formula I' are used in which
- $R^{6'}$, $R^{7'}$, $R^9$, $R^{11}$, $R^{14}$, $R^{15}$, $R^{15'}$ and $R^{16}$ in each case stand for a hydrogen atom, or $R^{6'}$, $R^{7'}$, $R^{14}$, $R^{15}$, $R^{15'}$ and $R^{16}$ in each case stand for a hydrogen atom, and $R^9$ and $R^{11}$ together stand for an additional bond, and all other substituents have the meanings that are indicated in claim 1.

If the estratriene derivatives of general formula I' contain additional double bonds in the B-, C- and/or D-ring, then a double bond is preferably in position 9(11), 14(15) or 15(16) or two double bonds are present in positions 9(11) and 14(15) or 15(16).

Another variant of the invention are estratriene derivatives of general formula I' in which
- $R^{17}$ and $R^{17'}$ are a group $R^{18}$—O— and a group $R^{18}$—; a group $R^{18}$— and a group —O—C(O)$R^{22}$, with $R^{18}$ and $R^{22}$ in each case in the meaning that is indicated under $R^2$.

Of the last-mentioned, in turn those gonatriene derivatives are preferred in which
- $R^{17}$ and $R^{17'}$ are a hydroxy group and a hydrogen atom, a $C_1$-$C_4$-alkyl group or $C_2$-$C_4$-alkenyl group and especially preferred are those in which
- $R^{17}$ and $R^{17'}$ are a hydroxy group and a hydrogen atom, a methyl, ethinyl or prop-1-inyl group.

Finally, an embodiment exists in that $R^{16'}$ stands for a group $R^{18}$—O— or $R^{19}SO_2$—O— with $R^{18}$ and $R^{19}$ in each case in the meaning that is indicated under $R^2$; $R^{17}$ and $R^{17'}$ each stand for a hydrogen atom and all other substituents can have the meanings that are indicated in general formula I'.

Preferred according to this invention is the use of one or more of the following compounds:
8β-Methyl-estra-1,3,5(10),9(11)-tetraene-3,17β-diol
3-methoxy-8β-methyl-estra-1,3,5(10),9(11)-tetraen-17β-ol
8β-methyl-estra-1,3,5(10)-triene-3,17β-diol
3-methoxy-8β-methyl-estra-1,3,5(10)-trien-17β-ol
8β-vinyl-estra-1,3,5(10),9(11)-tetraene-3,17β-diol
3-methoxy-8β-vinyl-estra-1,3,5(10),9(11)-tetraen-17β-ol 8β-(2',2'-difluorovinyl)-estra-1,3,5(10),9(11)-tetraene-3, 17β-diol
8β-(2',2'-difluorovinyl)-3-methoxy-estra-1,3,5(10),9(11)-tetraen-17β-ol
8β-vinyl-estra-1,3,5(10)-triene-3,17β-diol
3-methoxy-8β-vinyl-estra-1,3,5(10)-trien-17β-ol
8β-(2',2'-difluorovinyl)-estra-1,3,5(10)-triene-3,17β-diol
8β-(2',2'-difluorovinyl)-3-methoxy-estra-1,3,5(10)-trien-17β-ol
8β-ethyl-estra-1,3,5(10)-triene-3,17β-diol
8β-ethyl-3-methoxy-estra-1,3,5(10)-trien-17β-ol
8β-vinyl-estradiol-3-sulfamate
8β-vinyl-estradiol-3,17-disulfamate
8β-vinyl-estradiol-3-(N-acetyl)-sulfamate
8β-vinyl-estrone-3-sulfamate
8β-vinyl-estron-3-acetate
8β-vinyl-estriol
8β-vinyl-estriol-3-sulfamate
8β-methyl-estrone-3-sulfamate
8β-methyl-estriol
8β-(prop-(Z)-enyl)-estradiol
8β-(n-propyl)-estradiol
8β-ethinyl-estradiol
17α-ethinyl-8β-vinyl-estra-1,3,5(10)-triene-3,17β-diol
17α-methyl-8β-vinyl-estra-1,3,5,(10)-triene-3,17β-diol
16α-fluoro-8β-methyl-estra-1,3,5(10)-triene-3,17β-diol
8β-vinyl-estra-1,3,5(10)-triene-3,17α-diol
8β-methyl-estra-1,3,5(10)-triene-3,17α-diol
8β-vinyl-estradiol-diacetate
8β-methyl-estradiol-diacetate
8β-vinyl-estradiol-17-valerianate
17β-acetoxy-8β-vinyl-estra-1,3,5(10)-trien-3-ol
8β-vinyl-9β-estra-1,3,5(10)-triene-3,17β-diol
8β-ethyl-9β-estra-1,3,5(10)-triene-3,17β-diol.

Other possible configurations of this invention will emerge from the subclaims.

In addition to the above use of the compounds of general formula I', the invention also relates to the compounds of general formula I itself. These are the compounds of general formula I' excluding the compounds of general formula I', in which $R^3$ is a hydroxy, methoxy or acetyl group, and simultaneously $R^2$ represents a hydrogen atom, $R^6$, $R^{6'}$, $R^7$ and $R^{7'}$ in each case represent a hydrogen atom;

$R^8$ represents a methyl group, $R^9$ represents a hydrogen atom or $R^9$ and $R^{11}$ together represent an additional bond, $R^{11'}$ and $R^{12}$ in each case represent a hydrogen atom, $R^{14}$, $R^{15}$, $R^{15'}$, $R^{16}$ and $R^{16'}$ in each case represent a hydrogen atom, and $R^{17}$ and $R^{17'}$ stands for a β-hydroxy group and a hydrogen atom; for a β-(2-bromoacetyl)oxy group and a hydrogen atom; for a β-acetyl group and a hydrogen atom; a β-carboxyl group and a hydrogen atom; or $R^{17}$ and $R^{17'}$ together represent an oxygen atom.

This group of compounds that is disclaimed from the scope of general formula I' is already known from the following patent and bibliographic references:

FR M2743
Los, Marinus; U.S. Pat. No. 3,806,546
Los, Marinus; U.S. Pat. No. 3,736,345
Los, Marinus; U.S. Pat. No. 3,681,407
Los, Marinus; U.S. Pat. No. 3,501,530
Nagata, Wataru; Itazaki, Hiroshi; JP 45024573
Nagata, Wataru; Itazaki, Hiroshi; Takegawa, Bunichi; JP 45024139
Nagata, Wataru; Aoki, Tsutomu; Itazaki, Hiroshi; JP 45004060
Nagata, Wataru; Aoki, Tsutomu; Itazaki, Hiroshi; JP 45004059
Nagata, Wataru; Aoki, Tsutomu; Itazaki, Hiroshi; JP 45004058
Sakai, Kiyoshi; Amemiya, Shigeo; Chem. Pharm. Bull. (1970), 18(3), 641-3
Yoshioka, Kouichi; Goto, Giichi; Hiraga, Kentaro; Miki, Takuichi; Chem. Pharm. Bull. (1973), 21(11), 2427-31
Tori, K.; Editor(s): James, Vivian H. T.: Horm. Steroids, Proc. Int. Congr., 3rd (1971), Meeting Date 1970, 205-13
Tsukuda, Yoshisuke; Sato, Tomohiro; Shiro, Motoo; Koyama, Hirozo; J. Chem. Soc. B (1969), (4), 336-41
Tsukuda, Yoshiko; Itazaki, Hiroshi; Nagata, Wataru; Sato, Tomohiro; Shiro, Motoo; Koyama, Hirozo; Chem. Ind. (London) (1967), (48), 2047-8
Nakai, Hisayoshi; Koyama, Hirozo; Acta Crystallogr. (1967), 23(4), 674.

A selective estrogenic action and the use of the known compounds in terms of this invention have not yet been described, however.

In most cases, the already known estratrienes are described as intermediate compounds, as estrogens in the conventional sense or for use in analytical processes.

In the compounds of general formulas I and I' and in partial structures II and II' that are described below, a fluorine, chlorine, bromine or iodine atom can always stand for a halogen atom; a fluorine atom is preferred in each case. For the 11β-position, in particular also a chlorine atom can be named as a substituent. In particular, the hydrocarbon radicals, which can be partially or completely halogenated, are fluorinated radicals.

Hydrocarbon radical $R^{18}$ is, for example, a methyl, ethyl, propyl, isopropyl, butyl, isobutyl, tert-butyl, pentyl, isopentyl, neopentyl, heptyl or hexyl radical.

Alkoxy groups $OR^{18}$ in the compounds of general formulas I and I' and in partial structures II and II' that are described below can contain 1 to 6 carbon atoms in each case, whereby methoxy, ethoxy, propoxy, isopropoxy and t-butyloxy groups are preferred.

Representatives of the $C_1$-$C_5$-alkyl radicals $R^{20}$ and $R^{21}$ are methyl, ethyl, propyl, isopropyl, butyl, isobutyl, tert-butyl, pentyl, isopentyl and neopentyl.

As representatives of straight-chain or branched-chain hydrocarbon radicals $R^{22}$ with 1 to a maximum of 10 carbon atoms, for example, methyl, ethyl, propyl, isopropyl, butyl, isobutyl, tert-butyl, pentyl, isopentyl, neopentyl, heptyl, hexyl, and decyl can be mentioned; methyl, ethyl, propyl and isopropyl are preferred.

As perfluorinated alkyl groups, for example, trifluoromethyl, pentafluorethyl and nonafluorobutyl can be mentioned. Representatives of the partially fluorinated alkyl groups are, for example, 2,2,2-trifluoroethyl, 5,5,5,4,4-pentafluoropentyl, 6,6,6,5,5,4,4,3,3-nonafluorohexyl, etc.

As a $C_3$-$C_7$-cycloalkyl group, a cyclopropyl, butyl, pentyl, hexyl or heptyl group can be mentioned.

A $C_4$-$C_{15}$-cycloalkylalkyl radical has 3 to 7 carbon atoms in the cycloalkyl portion; typical representatives are the cycloalkyl groups that are mentioned directly above. The alkyl portion has up to 8 carbon atoms.

As examples of a $C_4$-$C_{15}$-cycloalkylalkyl radical, the cyclopropylmethyl, cyclopropylethyl, cyclopentylmethyl, cyclopentylpropyl group, etc., can be mentioned.

In terms of this invention, an aryl radical is a phenyl, 1- or 2-naphthyl radical; the phenyl radical is preferred.

Aryl always also includes a heteroaryl radical. Examples of a heteroaryl radical are the 2-, 3- or 4-pyridinyl, the 2- or 3-furyl, the 2- or 3-thienyl, the 2- or 3-pyrrolyl, the 2-, 4- or 5-imidazolyl, the pyrazinyl, the 2-, 4- or 5-pyrimidinyl or 3- or 4-pyridazinyl radical.

As substituents for an aryl or heteroaryl radical, for example, a methyl-, ethyl-, trifluoromethyl-, pentafluoroethyl-, trifluoromethylthio-, methoxy-, ethoxy-, nitro-, cyano-, halogen- (fluorine, chlorine, bromine, iodine), hydroxy-, amino-, mono($C_{1-8}$-alkyl)- or di($C_{1-8}$-alkyl)amino, whereby both alkyl groups are identical or different, di(aralkyl)amino, whereby both aralkyl groups are identical or different, can be mentioned.

An aralkyl radical is a radical that contains in the ring up to 14, preferably 6 to 10, C atoms and in the alkyl chain 1 to 8, preferably 1 to 4, C atoms. Thus, as aralkyl radicals, for example, benzyl, phenylethyl, naphthylmethyl, naphthylethyl, furylmethyl, thienylethyl, and pyridylpropyl are suitable. The rings can be substituted in one or more places by halogen, OH, O-alkyl, $CO_2H$, $CO_2$-alkyl, —$NO_2$, —$N_3$, —CN, $C_1$-$C_{20}$-alkyl, $C_1$-$C_{20}$-acyl, or $C_1$-$C_{20}$-acyloxy groups.

The alkyl groups or hydrocarbon radicals can be partially or completely fluorinated or substituted by 1-5 halogen atoms, hydroxy groups or $C_1$-$C_4$-alkoxy groups.

A vinyl or allyl radical is primarily defined with a $C_2$-$C_5$-alkenyl radical.

Other variants of the invention provide one or more, optionally conjugated double bonds in rings B, C and D of the estratriene skeleton, specifically one or more double bonds in positions 6, 7; 7, 8; 9, 11; 11, 12; 14, 15 and 15, 16. In this case, a double bond in position 7, 8 or in position 11, 12 or two double bonds in positions 6, 7 and 8, 9 are preferred (i.e., the naphthalene system is formed together with the aromatic A-ring).

One or more hydroxyl groups at C atoms 3, 16 and 17 can be esterified with an aliphatic, straight-chain or branched-chain, saturated or unsaturated $C_1$-$C_{14}$-mono- or polycarboxylic acid or an aromatic carboxylic acid or with an α- or β-amino acid.

Suitable as such carboxylic acids for esterification are, for example:

Monocarboxylic acids: formic acid, acetic acid, propionic acid, butyric acid, isobutyric acid, valeric acid, isovaleric acid, pivalic acid, lauric acid, myristic acid, acrylic acid, propiolic acid, methacrylic acid, crotonic acid, isocrotonic acid, oleic acid, and elaidic acid.

Esterification with acetic acid, valeric acid or pivalic acid is preferred.

Dicarboxylic acids: oxalic acid, malonic acid, succinic acid, glutaric acid, adipic acid, pimelic acid, suberic acid, azelaic acid, sebacic acid, maleic acid, fumaric acid, muconic acid, citraconic acid, and mesaconic acid.

Aromatic carboxylic acids: benzoic acid, phthalic acid, isophthalic acid, terephthalic acid, naphthoic acid, o-, m- and p-toluic acid, hydratropic acid, atropic acid, cinnamic acid, nicotinic acid, and isonicotinic acid.

Esterification with benzoic acid is preferred.

As amino acids, the representatives of these classes of substances that are known sufficiently to one skilled in the art are suitable, for example, alanine, β-alanine, arginine, cysteine, cystine, glycine, histidine, leucine, isoleucine, phenylalanine, proline, etc.

Esterification with β-alanine is preferred.

Preferred according to this invention are the compounds below:

8β-vinyl-estra-1,3,5(10),9(11)-tetraene-3,17β-diol
3-methoxy-8β-vinyl-estra-1,3,5(10),9(11)-tetraen-17β-ol
8β-(2',2'-difluorovinyl)-estra-1,3,5(10),9(11)-tetraene-3,17β-diol
8β-(2',2'-difluorovinyl)-3-methoxy-estra-1,3,5(10),9(11)-tetraen-17β-ol
8β-vinyl-estra-1,3,5(10)-triene-3,17β-diol
3-methoxy-8β-vinyl-estra-1,3,5(10)-trien-17β-ol
8β-(2',2'-difluorovinyl)-estra-1,3,5(10)-triene-3,17β-diol
8β-(2',2'-difluorovinyl)-3-methoxy-estra-1,3,5(10)-trien-17β-ol
8β-ethyl-estra-1,3,5(10)-triene-3,17β-diol
8β-ethyl-3-methoxy-estra-1,3,5(10)-trien-17β-ol
8β-vinyl-estradiol-3-sulfamate
8β-vinyl-estradiol-3,17-disulfamate
8β-vinyl-estradiol-3-(N-acetyl)-sulfamate
8β-vinyl-estrone-3-sulfamate
8β-vinyl-estron-3-acetate
8β-vinyl-estriol
8β-vinyl-estriol-3-sulfamate
8β-methyl-estrone-3-sulfamate
8β-methyl-estriol
8β-(prop-(Z)-enyl)-estradiol
8β-(n-propyl)-estradiol
8β-ethinyl-estradiol
17α-ethinyl-8β-vinyl-estra-1,3,5(10)-triene-3,17β-diol
17α-methyl-8β-vinyl-estra-1,3,5,(10)-triene-3,17β-diol
16α-fluoro-8β-methyl-estra-1,3,5(10)-triene-3,17β-diol
8β-vinyl-estra-1,3,5(10)-triene-3,17α-diol
8β-methyl-estra-1,3,5(10)-triene-3,17α-diol
8β-vinyl-estradiol-diacetate
8β-methyl-estradiol-diacetate
8β-vinyl-estradiol-17-valerianate
17β-acetoxy-8β-vinyl-estra-1,3,5(10)-trien-3-ol
8β-vinyl-9β-estra-1,3,5(10)-triene-3,17β-diol
8β-ethyl-9β-estra-1,3,5(10)-triene-3,17β-diol.

Another aspect of this invention relates to the use of the structural part of Formula II (8β-subst.-estra-1,3,5(10) triene-structural part)

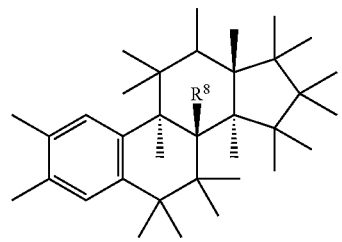

(II)

in which $R^8$ represents a straight-chain or branched-chain, optionally partially or completely halogenated alkyl or alkenyl radical with up to 5 carbon atoms, an ethinyl or prop-1-inyl radical, as a component of the total structure of compounds that have in vitro dissociation with respect to binding to estrogen receptor preparations of rat prostates and rat uteri, and especially as a component of the total structure of such compounds that have a dissociation in favor of their estrogenic action on bone rather than the uterus.

In addition to the aromatic A-ring, one or more double bonds can be present in the B-, C- and/or D-ring in positions 6(7); 9(11); 11(12); 14(15) and 15(16).

The possible substituents at carbon atoms 6, 7, 11, 15 and 16 can be respectively in α- or β-position.

This invention preferably relates to those structural parts of general formula II'

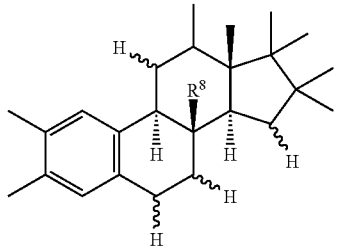

in which R⁸ represents a straight-chain or branched-chain, optionally partially or completely halogenated alkyl or alkenyl radical with up to 5 carbon atoms, an ethinyl or prop-1-inyl radical.

In the same manner, these structural parts can have one or more double bonds in the B-, C- and/or D-ring in addition to the aromatic A-ring.

The possible substituents at carbon atoms 6, 7, 11, 15, 16 and 17 can in turn be in α- or β-position in each case.

As prodrugs, the esters of the 8β-substituted estratrienes according to the invention have advantages compared to the unesterified active ingredients with respect to their method of administration, their type of action, strength and duration of action.

The sulfamates of 8β-substituted estratrienes according to the invention also have pharmacokinetic and pharmacodynamic advantages. Related effects were already described in other steroid-sulfamates (J. Steroid Biochem. Molec. Biol, 55, 395-403 (1995); Exp. Opinion Invest. Drugs 7, 575-589 (1998)).

In this patent application, steroids on which the 8β-substituted estra-1,3,5(10)triene skeleton is based are described for the treatment of estrogen receptor β-mediated diseases and conditions as selective estrogens, which have in vitro dissociation with respect to binding to estrogen receptor preparations of rat prostates and rat uteri and which have in vivo preferably a dissociation, for example, with respect to bone action rather than uterus action: these substances act in a bone-protective manner over a wide dose range without stimulating the uterus.

In addition, the substances in the male rat can have protective action against orchiectomy-induced bone mass loss, without inhibiting the secretion of pituitary hormones LH and FSH. Their liver action is small in the same dose range.

In addition, the substances exert an estrogen-like action on the vascular system and brain functions. Substances with higher binding to the rat prostate—compared to the rat uterus estrogen receptor—are more potent with respect to increasing the expression of serotonin receptors and transporters, in comparison to their positive effect on the LH release. Processes in whose regulation of neurotransmitters serotonin is involved are therefore advantageously influenced, and the compounds according to the invention exert an advantageous influence especially on mood and cognition.

They can be used as estrogens in the terms described in WO 97/45125 for the production of medications for influencing the level of serotonin or serotonin mRNA in humans.

It was found that the 8β-substituted estra-1,3,5(10)trienes according to the invention are suitable as selective estrogens for the treatment of various conditions and diseases that are characterized by a higher content of estrogen receptor β than estrogen receptor α in the corresponding target tissue or target organ.

The invention also relates to pharmaceutical preparations that contain at least one compound of general formula I (or physiologically compatible addition salts with organic and inorganic acids thereof) and the use of the compounds of general formula I' for the production of pharmaceutical agents, especially for the indications below.

The compounds can be used for the following indications after both oral and parenteral administration.

The novel selective estrogens that are described in this patent can be used as individual components in pharmaceutical preparations or in combination especially with antiestrogens or gestagens. Especially preferred is the combination of selective estrogens with ERα-selective antiestrogens, or with antiestrogens that are peripherally-selectively active, i.e., that do not pass through the blood-brain barriers.

The substances and the pharmaceutical agents that contain them are especially suitable for the treatment of peri- and postmenopausal symptoms, especially hot flashes, sleep disturbances, irritability, mood swings, incontinence, vaginal atrophy, and hormone-deficiency-induced emotional diseases. The substances for hormone substitution and the therapy of hormone-deficiency-induced symptoms in the case of surgical, medicinal or ovarian dysfunction that is caused in some other way are also suitable. Prevention of bone mass loss in postmenopausal women and male-menopausal men, in women who have undergone hysterectomies or in women who were treated with LHRH agonists or LHRH antagonists is also part of this.

The compounds are also suitable for alleviating symptoms of male menopause and female menopause, i.e., for male and female hormone replacement therapy (HRT), specifically both for prevention and for treatment, in addition for treatment of symptoms that are accompanied by a dysmenorrhea as well as for treatment of acne.

In addition, the substances can be used for prophylaxis against hormone-deficiency-induced bone mass loss and osteoporosis, for prevention of cardiovascular diseases, especially vascular diseases such as arteriosclerosis, for inhibition of the proliferation of arterial smooth muscle cells, for treatment of primary pulmonary high blood pressure and for prevention of hormone-deficiency-induced neurodegenerative diseases, such as Alzheimer's disease, as well as hormone-deficiency-induced impairment of memory and learning capacity.

In addition, the substances can be used for treatment of inflammatory diseases and diseases of the immune system, especially auto-immune diseases, such as, e.g., rheumatoid arthritis.

In addition, the compounds can be used for the treatment of male fertility disorders and prostatic diseases.

The compounds can also be used in combination with the natural vitamin D3 or with calcitriol analogues for bone formation or as supporting therapies to therapies that cause bone mass loss (for example, therapy with glucocorticoids, chemotherapy).

Finally, the compounds of general formula I' can be used in connection with progesterone receptor antagonists, specifically especially for use in hormone replacement therapy and for treatment of gynecological disorders.

A therapeutic product that contains an estrogen and a pure antiestrogen for simultaneous, sequential or separate use for the selective estrogen therapy of perimenopausal or postmenopausal conditions is already described in EP-A 0 346 014.

The amount of a compound of general formula I' that is to be administered varies within a wide range and can cover any effective amount. On the basis of the condition that is to be treated and the type of administration, the amount of the compound that is administered can be 0.01 µg/kg-10 mg/kg of body weight, preferably 0.04 µg/kg-1 mg/kg of body weight, per day.

In humans, this corresponds to a dose of 0.8 µg to 800 mg, preferably 3.2 µg to 80 mg, daily.

According to the invention, a dosage unit contains 1.6 µg to 200 mg of one or more compounds of general formula I'.

The compounds according to the invention and the acid addition salts are suitable for the production of pharmaceutical compositions and preparations. The pharmaceutical compositions or pharmaceutical agents contain as active ingredients one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., issued by Czetsch-Lindenwald, Hilfsstoffe für Pharmazie und angrenzende Gebiete [Adjuvants for Pharmaceutics and Related Fields]; Pharm. Ind., Issue,2, 1961, p. 72 and ff.: Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor KG, Aulendorf in Württemberg 1971.

The compounds can be administered orally or parenterally, for example intraperitoneally, intramuscularly, subcutaneously or percutaneously. The compounds can also be implanted in the tissue.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc.

For parenteral administration, the active ingredients can be dissolved or suspended in a physiologically compatible diluent. As diluents, very often oils with or without the addition of a solubilizer, a surfactant, a suspending agent or an emulsifying agent are used. Examples of oils that are used are olive oil, peanut oil, cottonseed oil, soybean oil, castor oil and sesame oil.

The compounds can also be used in the form of a depot injection or an implant preparation, which can be formulated so that a delayed release of active ingredient is made possible.

As inert materials, implants can contain, for example, biodegradable polymers, or synthetic silicones such as, for example, silicone rubber. In addition, for percutaneous administration, the active ingredients can be added to, for example, a patch.

For the production of intravaginal systems (e.g., vaginal rings) or intrauterine systems (e.g., pessaries, coils, IUDs, Mirena®) that are loaded with active compounds of general formula I' for local administration, various polymers are suitable, such as, for example, silicone polymers, ethylene vinyl acetate, polyethylene or polypropylene.

To achieve better bio-availability of the active ingredient, the compounds can also be formulated as cyclodextrin clathrates. For this purpose, the compounds are reacted with α-, β-, or γ-cyclodextrin or derivatives of the latter (PCT/EP95/02656).

According to the invention, the compounds of general formula I' can also be encapsulated with liposomes.

Methods

Estrogen Receptor Binding Studies

The binding affinity of the new selective estrogens was tested in competitive experiments with use of 3H-estradiol as a ligand to estrogen receptor preparations of rat prostates and rat uteri. The preparation of prostate cytosol and the estrogen receptor test with prostate cytosol was carried out as described by Testas et al. (1981) (Testas, J. et al., 1981, Endocrinology 109: 1287-1289).

The preparation of rat uterus cytosol as well as the receptor test with the ER-containing cytosol were basically performed as described by Stack and Gorski, 1985 (Stack, Gorski 1985, Endocrinology 117, 2024-2032) with some modifications as described in Fuhrmann et al. (1995) (Fuhrmann, U. et al. 1995, Contraception 51: 45-52).

The substances that are described in this patent have higher binding affinity to the estrogen receptor of rat prostates than to estrogen receptors of rat uteri. In this case, it is assumed that ERβ predominates in the rat prostates over ERα, and ERα predominates in rat uteri over ERβ. Table 1 shows that the ratio of the binding to prostate and uterus receptors qualitatively coincides with the quotient of relative binding affinity (RBA) to human ERβ and ERα of rats (according to Kuiper et al. (1996), Endocrinology 138: 863-870) (Table 1).

TABLE 1

| Estrogen | hERα RBA* | hERβ RBA* | ERβ/ERα | Rat uterus ER (RBA) | Rat prost. ER (RBA) | prost. ER/uterus ER |
|---|---|---|---|---|---|---|
| Estradiol | 100 | 100 | 1 | 100 | 100 | 1 |
| Estrone | 60 | 37 | 0.6 | 3 | 2 | 0.8 |
| 17α-Estradiol | 58 | 11 | 0.2 | 2.4 | 1.3 | 0.5 |
| Estriol | 14 | 21 | 1.5 | 4 | 20 | 5 |
| 5-Androstenediol | 6 | 17 | 3 | 0.1 | 5 | 50 |
| Genisteine | 5 | 36 | 7 | 0.1 | 10 | 100 |
| Coumestrol | 94 | 185 | 2 | 1.3 | 24 | 18 |

*Cited from: Kuiper et al. (1996), Endocrinology 138: 863-870

Table 2 shows the results for the compound 8β-methyl-estra-1,3,5(10)-triene-3,17β-diol (compound D) that is to be used according to the invention as well as for the compounds according to the invention 8β-Vinyl-estra-1,3,5(10),9(11)-tetraene-3,17β-diol (A)

8β-vinyl-estra-1,3,5(10)-triene-3,17β-diol (B)

8β-(2,2-difluorovinyl)-estra-1,3,5(10)-triene-3,17β-diol (C) and

8β-ethyl-estra-1,3,5(10)-triene-3,17β-diol (E).

TABLE 2

| Compound | RBA Rat Uterus | RBA Rat Prostate |
|---|---|---|
| 8β-Vinyl-estra-1,3,5(10),9(11)-tetraene-3,17β-diol (A) | 1 | 83 |

TABLE 2-continued

| Compound | RBA Rat Uterus | RBA Rat Prostate |
|---|---|---|
| 8β-Vinyl-estra-1,3,5(10)-triene-3,17β-diol (B) | 0.7 | 63 |
| 8β-(2,2-Difluorovinyl)-estra-1,3,5(10)-triene-3,17β-diol (C) | 0.9 | 5 |
| 8β-Methyl-estra-1,3,5(10)-triene-3,17β-diol (D) | 1.3 | 67 |
| 8β-Ethyl-estra-1,3,5(10)-triene-3,17β-diol (E) | <0.3 | 7 |

Compounds A, B, C, D and E show a higher binding affinity to the estrogen receptor of rat prostates than to the estrogen receptor of rat uteri.

In addition, the predictability of the 'prostate-ER versus the uterus-ER test system' was confirmed with respect to tissue-selective action by in vivo studies. Substances with a preference for prostate-ER are dissociated in vivo preferably with respect to bone and uterus action in favor of action on bones. In addition, substances with higher binding to the rat prostate—compared to the rat uterus estrogen receptor—are more potent with respect to increasing the expression of serotonin receptors and transporters, in comparison to their positive effect on the LH release.

Bone Studies

Three-month-old female rats are ovariectomized and treated once daily for 28 days with the test compound immediately after the operation. The administration is carried out subcutaneously in arachis oil/ethanol. The animals are sacrificed on the day after the last administration, and tibia as well as uteri are removed. The uteri are weighed, fixed and worked up for histological studies. The determination of bone density is carried out ex vivo on prepared long bones by means of pQCT (quantitative computer tomography). The measurements are made at a distance of 4-6 mm from the ball of the joint of the proximal tibia.

The ovariectomy reduces the density of the trabecular bone in the measured area by about 400 mg of $Ca^{2+}/cm^3$ to about 300 mg of $Ca^{2+}/cm^3$. By treatment with a compound of general formula I according to this invention, the degradation of the bone density is prevented or inhibited. The bone density in the proximal tibia was measured.

The higher binding affinity to the estrogen receptor of rat prostates than to the estrogen receptor of rat uteri is reflected in vivo preferably in considerably lower amounts of the compounds according to the invention, which produce a 50% bone protection, in comparison to the amounts that produce a 50% uterus stimulation, relative to the bone mass loss, which can be measured in ovariectomized, untreated female rats 28 days after the ovariectomy unlike in intact animals that are subjected to sham operations.

The vascular action of the estrogens according to the invention is determined in the model of the ApoE-knockout mouse, as described by R. Elhage et al., 1997, as well as in the model of the balloon-catheter-induced vascular damage (restenosis model) (Elhage, R. et al. 1997, Arteriosclerosis, Thrombosis and Vascular Biology 17: 2679-2684).

To detect the action of estrogens on the brain function, the oxytocin-, oxytocin receptor- or vasopressin-mRNA expression is used as a surrogate parameter (Hrabovszky, E. et al. 1998, Endocrinology 1339: 2600-2604). Ovariectomized rats are treated for 7 days with the test substance or vehicle (administration: subcutaneous or oral, six times daily). On day 7 after the first administration, the animals are decapitated, the uterus weight is determined, and the oxytocin-, oxytocin receptor-, or vasopressin-mRNA level is studied by means of in situ hybridization in suitable brain sections. The $ED_{50}$ values are determined with respect to stimulation of uterus growth and induction of the oxytocin receptor mRNA.

Another possibility to demonstrate in vivo the dissociated estrogen action of the substances according to the invention consists in the fact that after a one-time administration of the substances in rats, effects on the expression of 5HT2a-receptor and serotonin transporter protein and mRNA levels in ERβ-rich brain areas can be measured. Compared to the effect on the serotonin receptor and transporter expression, the effect on the LH-secretion is measured. Substances with higher binding to the rat prostate—compared to the rat uterus estrogen receptor—are more potent with respect to increasing the expression of serotonin receptors and transporters, in comparison to their positive effect on the LH release. The density of serotonin receptors and transporters is determined in brain sections using radioactive ligands, and the corresponding mRNA is determined using in situ hybridization. The method is described in the literature: G. Fink & B. E. H. Sumner 1996 Nature 383: 306; B. E. H. Sumner et al. 1999 Molecular Brain Research, in press.

In accordance with their stronger binding to the rat prostate rather than the rat uterus estrogen receptor, substances A, B, C, D and E according to the invention result in an increased expression of the serotonin receptor and transporter.

Production of the Compounds According to the Invention

The compounds of general formula I (or I') according to the invention are produced as described in the examples. Additional compounds of general formula I' can be obtained by an analogous procedure using reagents that are homologous to the reagents that are described in the examples.

Etherification and/or esterification of free hydroxy groups is carried out according to methods that are common to one skilled in the art.

The compounds according to the invention can be present in carbon atoms 6, 7, 11, 15, 16 and 17 as α,β-stereoisomers. In the production of compounds according to the described processes, the compounds in most cases accumulate as mixtures of the corresponding α,β-isomers. The mixtures can be separated by, for example, chromatographic processes.

According to general formula I, possible substituents can already be present in final form or in the form of a precursor even in the starting product, a substituted estrone already corresponding to the desired end product.

The introduction of a substituent or reactive precursor on carbon atom 7 by nucleophilic addition of the substituent or precursor on a 6-vinylsulfone thus is possible (DE 42 18 743 A1). In this case, 7α- and 7β-substituted compounds, which can be separated by, for example, chromatographic processes, are obtained in different proportions, based on the reactants and the selected reaction conditions.

17-Substituents are also introduced according to known processes by nucleophilic addition of the desired substituent or a reactive precursor thereof and are optionally further built up.

The 8β-substituted estratriene-carboxylic acid esters according to the invention are produced from the corresponding hydroxy steroids analogously to processes that are also known (see, e.g., Pharmazeutische Wirkstoffe, Synthesen, Patente, Anwendungen [Pharmaceutical Active Ingredients, Syntheses, Patents, Applications]; A. Kleemann, J. Engel', Georg Thieme Verlag Stuttgart 1978, Arzneimittel, Fortschritte [Pharmaceutical Agents, Improvements] 1972 to 1985; A. Kleemann, E. Lindner, J. Engel (Editors), VCH 1987, pp. 773-814).

The estratriene-sulfamates according to the invention are available in a way that is known in the art from the corresponding hydroxy steroids by esterification with sulfamoyl chlorides in the presence of a base (Z. Chem. 15, 270-272 (1975); Steroids 61, 710-717 (1996)).

Subsequent acylation of the sulfamide group results in the (N-acyl)sulfamates according to the invention, for which pharmacokinetic advantages were already detected in the case of the absence of an 8-substituent (cf. DE 195 40 233 A1).

The regioselective esterification of polyhydroxylated steroids with N-substituted and N-unsubstituted sulfamoyl chlorides is carried out according to partial protection of those hydroxyl groups that are to remain unesterified. Silyl ethers have turned out to be protective groups with selective reactivity that is suitable for this purpose, since these silyl ethers are stable under the conditions of sulfamate formation, and the sulfamate group remains intact when the silyl ethers are cleaved again for regeneration of the residual hydroxyl group(s) still contained in the molecule (Steroids 61, 710-717 (1996)). The production of the sulfamates according to the invention with one or more additional hydroxyl groups in the molecule is also possible in that the starting material is suitable hydroxy-steroid ketones. First, depending on the goal, one or more hydroxyl groups that are present are subjected to sulfamoylation. Then, the sulfamate groups optionally can be converted with a desired acyl chloride in the presence of a base into the (N-acyl)sulfamates in question. The now present oxosulfamates or oxo-(N-acyl)sulfamates are converted by reduction into the corresponding hydroxysulfamates or hydroxy-(N-acyl) sulfamates (Steroids 61, 710-717 (1996)). Sodium borohydride and the borane-dimethyl sulfide complex are suitable as suitable reducing agents.

Functionalizations at carbon atom 2 are possible, for example, by electrophilic substitution after prior deprotonation of the 2-position of the corresponding 3-(2-tetrahydropyranyl)- or 3-methyl ether with a lithium base (e.g., methyllithium, butyllithium). Thus, for example, a fluorine atom can be introduced by reaction of the C—H-activated substrate with a fluorinating reagent such as N-fluoromethane sulfonimide (WO 94/24098).

The introduction of variable substituents in rings B, C and D of the estratriene skeleton can basically be carried out according to the chemical teaching that is known to one skilled in the art, with which the corresponding estratriene derivatives that are not substituted in 8-position are produced (see, i.a.: Steroide [Steroids], L. F. Fieser, M. Fieser, Verlag Chemie, Weinheim/Bergstr., 1961; Organic Reactions in Steroid Chemistry, J. Fried, J. A. Edwards, Van Nostrand Reinhold Company, New York, Cincinnati, Toronto, London, Melbourne, 1972; Medicinal Chemistry of Steroids, F. J. Zeelen, Elsevier, Amsterdam, Oxford, New York, Tokyo, 1990). This relates to, for example, the introduction of substituents, such as hydroxyl or alkyloxy groups, alkyl, alkenyl or alkinyl groups or halogen, especially fluorine.

Substituents according to general formula I can also be introduced in the stage of estratrienes that are already substituted in 8-position, however. This can be useful or necessary especially in the case of multiple substitutions of the desired final compound.

The examples below are used for a more detailed explanation of the invention.

The general synthesis routes for these examples are shown in figures 1 to 3.

As starting material for such syntheses, 11-keto-estratetraene derivatives of type 1 or 2 (U.S. Pat. No. 3,491,089, Tetrahedron Letters, 1967, 37, 3603), which are substituted stereoselectively in 8β-position in the reaction with diethylaluminum cyanide, are used. By subsequent reduction of the carbonyl function at C(11) and elimination of the hydroxyl group that is produced, 8β-substituted estra-1,3,5 (10),9(11)-tetraenes, which in turn can be converted into 8β-aldehydes, are obtained. A functionalization, e.g., by Wittig reactions with subsequent removal of protective groups, results in the 8β-steroids according to the invention.

The 11-oxidized estradiol derivatives that are first obtained in this sequence can be further reacted to many substitution patterns on the steroid like the double bond C(9)-C(11) according to methods that are known to one skilled in the art. For example, an 11α-hydroxy group can be converted into an 11β-fluorine atom according to the process that is described by Vorbrüggen et al.

For the production of the derivatives of 8β-substituted estra-1,3,5(10)-triene-3,16ξ-diols according to the invention without 17-substituents, mainly the following synthesis strategy is used. In this connection, the 8β-carbonyl function is protected as an acetal. After subsequent oxidation, the 17-ketosteroid can be converted into a sulfonylhydrazone, in the simplest case by reaction with phenylsulfonyl hydrazide. By a degradation reaction, the formation of the C(16)-C(17) olefin is carried out (Z. Chem. 1970, 10, 221-2; Liebigs Ann. Chem. 1981, 1973-81), on which hypobromide is stored in a regio/stereocontrolled way. Reductive dehalogenation and removal of the acetal protective group at 8β opens the way for transformations to the compounds according to the invention. The 16β-alcohols that can be obtained according to this method can be converted into the 16α-epimer by known methods (Synthesis 1980, 1).

Another variant for the introduction of the hydroxyl group at C-atom 16 consists in the hydroboration of the 16(17)-double bond with sterically exacting boranes. Of this reaction, it is known that it results in 16-oxidized products (Indian J. Chem. 1971, 9, 287-8). The reaction of the estra-1,3,5(10),16-tetraene 17 with 9-borabicyclo[3.3.1] nonane after the oxidation with alkaline hydrogen peroxide consequently produces 16α-hydroxyestratrienes. The epimeric 16β-hydroxy steroids are formed to a lesser extent in this reaction. Further transformations on the 8β-substituent then result in the compounds of general formula I according to the invention.

Characteristic, but not limiting synthesis processes, which are useful for providing representative substitution patterns on the estrone skeleton, also in combination with several substituents, are found in, for example: C(1) J. Chem. Soc. (C) 1968, 2915; C(7) Steroids 54, 1989, 71; C(8α) Tetrahedron Letters 1991, 743; C(8β) Tetrahedron Letters 1964, 1763; J. Org. Chem. 1970, 35, 468; C(11) J. Steroid Biochem. 31, 1988, 549; Tetrahedron 33, 1977, 609 and J. Org. Chem. 60, 1995, 5316; C(9) DE-OS 2035879; J. Chem. Soc. Perk. 1 1973, 2095; C(15) J. Chem. Soc. Perk. 1 1996, 1269.); C(13α) Mendeleev Commun. 1994, 187; C(14β) Z. Chem. 23, 1983, 410.

In the examples and in the figures, the following abbreviations apply:

THF=tetrahydrofuran;   THP=tetrahydropyran-2-yl;
  DHP=dihydropyran;   DMSO=dimethyl   sulfoxide;

MTBE=methyl-tert-butyl ether; DIBAH=diisobutyl-aluminum hydride; LTBAH=lithium-tri-tert.-butoxy-aluminum hydride.

EXAMPLE 1

3-methoxy-17β-(tetrahydropyran-2-yloxy)-estra-1,3, 5(10),8-tetraen-11-one (2)

47 ml of dihydropyran and 0.96 g of pyridine toluenesu-fonate were added at room temperature to 15.29 g of 11-keto-3-methoxy-estra-1,3,5(10),8-tetraen-17β-ol (1) in 35 ml of dichloromethane, and it was stirred for 2 hours. Then, the reaction solution was shaken several times with saturated sodium bicarbonate solution, washed with water and dried with magnesium sulfate. The solvent was evaporated in a vacuum, and the residue was purified on silica gel (solvent mixture: cyclohexane/ethyl acetate=8/2). 16.8 g (83%) of light yellowish, viscous oil was thus obtained.

8β-cyano-3-methoxy-17β-(tetrahydropyran-2-yloxy)-estra-1,3,5(10)-trien-11-one (3)

195 ml of diethylaluminum cyanide (1.0 M, in toluene) was added in drops at a temperature of −5° C. under argon to a solution of 24.5 g of 11-ketosteroid 2 in 330 ml of toluene, and it was stirred for 1.5 hours while cooling was continued. Then, the mixture was poured onto 470 ml of ice-cooled 1N sodium hydroxide solution, stirred for 1 hour, extracted several times with ethyl acetate, and the collected organic phases were washed with water and brine and dried with magnesium sulfate. The chromatography of the evaporation residue on silica gel (solvent mixture: cyclohexane/ethyl acetate=4/1) yielded 3 as a foam in a yield of a total of 12.0 g (37%).

8β-cyano-3-methoxy-17β-(tetrahydropyran-2-yloxy)-estra-1,3,5(10)-trien-11-ol (4)

A solution of 33.1 g of steroid 3 in 400 ml of THF was cooled to 0° C., mixed in portions with 51.0 g of LTBAH, and the solution was stirred for 1 hour while cooling was continued and for 1 hour at room temperature. 25 ml of saturated sodium bicarbonate solution was added in drops to the reaction solution at 0° C., the precipitate that was produced was separated by filtration on Celite, and the filtrate was concentrated by evaporation to a very large extent. The residue was extracted several times with ethyl acetate, the collected organic phases were then washed with brine, dried on magnesium sulfate, and the solvent was removed in a vacuum. In this way, 27.6 g (97%) of foamy 4 was obtained, which was used without further purification in the next stage.

8-cyano-3-methoxy-17β-(tetrahydropyran-2-yloxy)-estra-1,3,5(10),9(11)-tetraene (5)

27.6 ml of phosphorus oxychloride was added in drops to a solution of 27.6 g of 4 in 275 ml of pyridine at a temperature of 0-5° C., and it was stirred for another 1.5 hours at this temperature. Then, the mixture was moved into a dropping funnel and added in drops to an ice-cooled, saturated sodium bicarbonate solution. Then, it was extracted with dichloromethane, the collected organic phases were washed with brine, dried on magnesium sulfate, and the solvent was removed in a vacuum. In this way, 23.5 g (89%) of almost colorless, foamy 5 was obtained, which was used without further purification in the next stage.

8β-carbonyl-3-methoxy-estra-1,3,5(10),9(11)-tetraen-17β-ol (6)

A solution of 41 ml of DIBAH in 100 ml of toluene was added in drops to 11.4 g of 8β-cyano-steroid 5 in 70 ml of toluene under argon at 0° C., and it was stirred for 1.5 hours at this temperature. The solution was mixed at 0° C. in succession with 33 ml of ethanol, 33 ml of ethanol-water mixture (v/v=1/1) and 120 ml of semi-concentrated hydrochloric acid, and then refluxed for 2 hours. The mixture was extracted several times with ethyl acetate, the collected organic phases were washed with water, dried with magnesium sulfate and evaporated to the dry state in a vacuum. By chromatography of the residue on silica gel (solvent mixture: cyclohexane/ethyl acetate=3/2), 3.21 g (35%) of foamy 6 was obtained.

3-methoxy-8β-methyl-estra-1,3,5(10),9(11)-tetraen-17β-ol (7a)

0.18 ml of hydrazinium hydroxide (80%, with water) and 50 mg of 8β-carbonyl-3-methoxy-estra-1,3,5(10),9(11)-tetraen-17β-ol (6) in 6.5 ml of triethylene glycol were added to a solution of 225 mg of potassium hydroxide in 3.5 ml of triethylene glycol at room temperature and heated for 2 hours to 200° C. After cooling, it was mixed in succession with 10 ml of water and 3 ml of 10% sulfuric acid. The mixture was extracted several times with ether, the collected organic phases were washed with water, dried with magnesium sulfate and evaporated to the dry state in a rotary evaporator. The chromatography of the residue on silica gel (solvent mixture: cyclohexane/ethyl acetate=8/2) yielded 36 mg (79%) of 3-methoxy-8β-methyl-estra-1,3,5(10),9(11)-tetraen-17β-ol with a melting point of 168° C.

EXAMPLE 2

The synthesis of substance 7a was described under Example 1, 1.1-1.6.

3-methoxy-8β-methyl-estra-1,3,5(10)-trien-17β-ol (8a)

75 mg of 3-methoxy-8β-methyl-estra-1,3,5(10),9(11)-tetraen-17β-ol (7a) was dissolved in a solvent mixture that consists of 3.5 ml of THF and 1.5 ml of methanol and stirred with 75 mg of palladium (10%, on magnesium carbonate) for 3.75 hours at room temperature under hydrogen atmosphere. Then, the reaction solution was filtered on Celite, the filtrate was evaporated to the dry state in a rotary evaporator, and the thus obtained TLC-uniform, foamy product (74 mg, 98%) was used without further purification in the next stage.

8β-methyl-estra-1,3,5(10)-triene-3,17β-diol (8b)

74 mg of 3-methoxy-8β-methyl-estra-1,3,5(10)-trien-17β-ol was dissolved in 3 ml of anhydrous toluene, cooled to 0° C. and mixed carefully under argon with 0.6 ml of DIBAH. The reaction mixture was slowly refluxed, and it was kept at this temperature for 3.5 hours. Then, it was cooled again to 0° C., the solution was mixed in succession with 2 ml of ethanol, 2 ml of ethanol-water mixture (v/v=1/1) and 2 ml of semi-concentrated hydrochloric acid and extracted several times with ethyl acetate. The collected organic phases were washed neutral with water, dried with magnesium sulfate and evaporated to the dry state in a vacuum. 70 mg (99%) of colorless crystals with a melting point of 168-170° C. was obtained.

EXAMPLE 3

The synthesis of substance 6 was described under Example 1, 1.1-1.5.

8β-carbonyl-3-methoxy-17β-(tetrahydropyran-2-yloxy)-estra-1,3,5(10),9(11)-tetraene (9)

A solution of 500 mg of 6 in 10 ml of dichloromethane was mixed with 1.45 ml of 3,4-dihydro-2H-pyran and 28 mg (0.11 mmol) of pyridine toluenesulfonate and stirred for 16 hours at room temperature. The mixture was washed in succession several times with saturated sodium bicarbonate solution and water, and the organic phase was evaporated to the dry state in a vacuum after drying with magnesium sulfate. Product 9 accumulated as a foam in a yield of 527 mg (86%).

3-methoxy-17β-(tetrahydropyran-2-yloxy)-8β-vinyl-estra-1,3,5(10),9(11)-tetraene (10a)

A solution of 585 mg of 8β-carbonyl-3-methoxy-17β-(tetrahydropyran-2-yloxy)-estra-1,3,5(10),9(11)-tetraene in 25 ml of DMSO was mixed under argon first with 4.92 g of methyltriphenylphosphonium bromide, then carefully with 394 mg of sodium hydride (80%, in paraffin oil), and then heated for 2 hours slowly to an internal temperature of 55° C. After cooling, 25 ml of water was added in drops, extracted several times with diethyl ether, washed with water, and the collected organic phases were dried with magnesium sulfate. After the solvent was removed, the residue was purified by chromatography on silica gel (solvent mixture: cyclohexane/MTBE=30/1). 520 mg (89%) of 8β-vinyl steroid in the form of a colorless foam was obtained.

8β-vinyl-estra-1,3,5(10),9(11)-tetraene-3,17β-diol (11a)

550 mg of 3-methoxy-17β-(tetrahydropyran-2-yloxy)-8β-vinyl-estra-1,3,5(10),9(11)-tetraene was reacted according to general operating instructions 19. The yield of colorless crystals with a melting point of 149-150° C. was 315 mg (76%).

8β-(2,2-difluorovinyl)-3-methoxy-17β-(tetrahydropyran-2-yloxy)-estra-1,3,5(10),9(11)-tetraene (10b)

A solution of 0.22 ml of diethyl(difluoromethyl)phosphonate in 0.4 ml of n-pentane and 2 ml of 1,2-dimethoxyethane were cooled under argon to −78° C., mixed with 0.82 ml of tert-butyllithium solution (1.7 M, in n-pentane) and stirred for 0.25 hour at this temperature. At the same temperature, a solution of 220 mg of 8β-carbonyl-3-methoxy-17β-(tetrahydropyran-2-yloxy)-estra-1,3,5(10),9(11)-tetraene in 3.5 ml of 1,2-dimethoxyethane and 0.58 ml of n-pentane were now added in drops and stirred for 0.5 hour with continued cooling. Then, it was heated first to room temperature and then heated for 1 hour to an internal temperature of 84° C. while the n-pentane was distilled off. After cooling, the batch was poured onto 20 ml of ice water, light brown precipitate was filtered off, it was extracted with dichloromethane, and the collected organic phases were dried with magnesium sulfate. After the solvent was removed, the residue was purified by chromatography on silica gel (solvent mixture: cyclohexane/MTBE=30/1). The yield of oily, almost colorless steroid was 108 mg (46%).

8β-(2,2-difluorovinyl)-estra-1,3,5(10),9(11)-tetraene-3,17β-diol (11b)

105 mg of 8β-(2,2-difluorovinyl)-3-methoxy-17β-(tetrahydropyran-2-yloxy)-estra-1,3,5(10),9(11)-tetraene was reacted according to general operating instructions 19 for ether cleavage with DIBAH/acid. The yield of colorless crystals with a melting point of 103-106° C. was 75 mg (93%).

EXAMPLE 4

The synthesis of substance 9 was described under Example 3, 3.1.

8β-carbonyl-3-methoxy-17β-(tetrahydropyran-2-yloxy)-estra-1,3,5(10)-triene (12)

1.73 g of 9 was dissolved in 75 ml of solvent mixture that consists of THF and methanol (v/v=7/3) and stirred with 1.0 g of palladium (10%, on magnesium carbonate) for 3.75 hours at room temperature under hydrogen atmosphere. Then, the reaction solution was filtered on Celite, the filtrate was evaporated to the dry state in a rotary evaporator, and the thus obtained TLC-uniform, bright oil was used without additional purification for other reactions.

3-methoxy-17β-(tetrahydropyran-2-yloxy)-8β-vinyl-estra-1,3,5(10)-triene (13a)

A solution of 2.47 g of 8β-carbonyl-3-methoxy-17β-(tetrahydropyran-2-yloxy)-estra-1,3,5(10),9(11)-tetraene in 100 ml of DMSO was mixed under argon first with 19.80 g of methyltriphenylphosphonium bromide, then carefully with 1.58 g of sodium hydride (80%, in paraffin oil), and then heated slowly for 2 hours to an internal temperature of 55° C. After cooling, 100 ml of water was added in drops, extracted several times with diethyl ether, washed with water, and the collected, organic phases were dried with magnesium sulfate. After the solvent was removed, the residue was purified by chromatography on silica gel (solvent mixture: cyclohexane/MTBE=30/1). 1.91 g (78%) of 8β-vinyl steroid was obtained as a colorless foam.

8β-vinyl-estra-1,3,5(10)-triene-3,17β-diol (14a)

1.86 g of 3-methoxy-17β-(tetrahydropyran-2-yloxy)-8β-vinyl-estra-1,3,5(10)-triene was reacted according to general operating instructions 19. The crude 8β-vinyl-estra-1,3,5(10)-triene-3,17β-diol was obtained after purification on silica gel (solvent mixture: cyclohexane/ethyl acetate=7/3) in the form of colorless crystals with a melting point of 163-165° C. in a yield of 1.20 g (86%).

8β-(2,2-difluorovinyl)-3-methoxy-17β-(tetrahydropyran-2-yloxy)-estra-1,3,5(10)-triene (13b)

A solution of 0.6 ml of diethyl(difluoromethyl)phosphonate in 1.0 ml of n-pentane and 5.6 ml of 1,2-dimethoxyethane were cooled under argon to −78° C., mixed with 2.2 ml of tert-butyllithium solution (1.7 M, in n-pentane) and stirred for 0.25 hour at this temperature. At the same temperature, a solution of 600 mg of 8β-carbonyl-3-methoxy-17β-(tetrahydropyran-2-yloxy)-estra-1,3,5(10),9(11)-tetraene in 9.2 ml of 1,2-dimethoxyethane and 1.6 ml of n-pentane were now added in drops and stirred for 0.5 hour with continued cooling. Then, it was heated first to room temperature and then heated for 1 hour to an internal temperature of 84° C. while the n-pentane was distilled off. After cooling, the batch was poured onto 40 ml of ice water, light brown precipitate was filtered off, it was extracted with dichloromethane, and the collected organic phases were dried with magnesium sulfate. After the solvent was removed, the residue was purified by chromatography on silica gel (solvent mixture: cyclohexane/MTBE=30/1). The yield of oily, almost colorless steroid was 75 mg (12%).

8β-(2,2-difluorovinyl)-estra-1,3,5(10)-triene-3,17β-diol (14b)

According to general operating instructions 19., 78 mg of 3-methoxy-8β-(2,2-difluorovinyl)-17β-(tetrahydropyran-2-yloxy)-estra-1,3,5(10)-triene was reacted. The yield of colorless crystals with a melting point of 154-156° C. was 56 mg (90%).

EXAMPLE 5

The synthesis of substance 13a was described under Examples 4, 4.2.

8β-ethyl-3-methoxy-17β-(tetrahydropyran-2-yloxy)-estra-1,3,5(10)-triene 0.50 g of 13a was dissolved in 25 ml of solvent mixture that consists of THF and methanol (v/v=7/3) and stirred with 0.30 g of palladium (10% on magnesium carbonate) for 3.75 hours at room temperature under hydrogen atmosphere. Then, the reaction solution was filtered on Celite, the filtrate was evaporated to the dry state in a rotary evaporator and the bright foam that was obtained was used without additional purification in the next stage.

8β-ethyl-estra-1,3,5(10)-triene-3,17β-diol (15a, 15b)

330 mg of crude 8β-ethyl-3-methoxy-17β-(tetrahydropyran-2-yloxy)-estra-1,3,5(10)-triene from the last stage was reacted according to general operating instructions 6.1 and 6.2. By, chromatography on silica gel, epimeric estratriene diols 15a and 15b in yields of 161 mg or 20 mg can be isolated from the accumulating crude product. The melting point for 15a is approximately 149-152° C. and that of 15b is approximately 185-187° C.

EXAMPLE 6

3-methoxy-8β-vinyl-estra-1,3,5(10)-trien-17-one

A solution of 700 mg of 3-methoxy-8β-vinyl-estra-1,3,5(10)-trien-17β-ol in 30 ml of dichloromethane was mixed with 740 mg of pyridinium chlorochromate and stirred for 3 hours at room temperature. By filtration of the reaction mixture on silica gel (solvent mixture: cyclohexane/ethyl acetate=7/3) and subsequent concentration by evaporation of the filtrate in a rotary evaporator, 680 mg (98%) of 3-methoxy-8β-vinyl-estra-1,3,5(10)-trien-17-one was obtained as almost colorless foam, which was used in the next stage without further purification.

3-hydroxy-8β-vinyl-estra-1,3,5(10)-trien-17-one 460 mg of 3-methoxy-8β-vinyl-estra-1,3,5(10)-trien-17-one was added to 9.2 g of pyridinium hydrochloride at 180° C. and stirred for 3 hours at the same temperature. Then, it was poured onto ice, the deposited precipitate was filtered off, washed with water and dried. The yield of 2-hydroxy-8β-vinyl-estra-1,3,5(10)-trien-17-one with a melting point of 239-242° C. amounted to 400 mg (90%).

EXAMPLE 7

3-sulfamoyloxy-8β-vinyl-estra-1,3,5(10)-trien-17-one 76 mg of 3-hydroxy-8β-vinyl-estra-1,3,5(10)-trien-17-one was dissolved in 7 ml of dichloromethane, mixed with 0.26 ml of 2,6-di-tert-butylpyridine and 221 mg of sulfamoyl chloride and stirred for 1.5 hours at room temperature. Then, the reaction mixture was added to water and extracted several times with dichloromethane. The collected organic phases were washed with saturated sodium chloride solution, dried on magnesium sulfate and concentrated by evaporation in a vacuum to the greatest extent possible. By chromatography of the residue that is obtained on silica gel (solvent mixture: cyclohexane/ethyl acetate=7/3), 46 mg (48%) of 17-oxo-8β-vinyl-estra-1,3,5(10)-trien-3-yl-amidosulfonate was obtained.

3-sulfamoyloxy-8β-vinyl-estra-1,3,5(10)-trien-17β-ol 46 mg of 17-oxo-8β-vinyl-estra-1,3,5(10)-trien-3-yl-amidosulfonate was dissolved in 1.5 ml of THF and 1.5 ml of methanol, mixed at 0° C. with 33 mg of sodium borohydride and stirred for 1 hour at 0° C. Then, 0.2 ml of concentrated acetic acid was added, and it was concentrated by evaporation in a vacuum. The residue was taken up in ethyl acetate and water, the organic phase was separated, and the aqueous was extracted several times with ethyl acetate. The collected organic phases were washed with saturated sodium chloride solution, dried on magnesium sulfate and concentrated by evaporation in a vacuum. The crude product was purified by chromatography on silica gel (solvent mixture: cyclohexane/ethyl acetate=6/4) and yielded 45 mg (98%) of 17β-hydroxy-8β-vinyl-estra-1,3,5(10)-trien-3-yl-amidosulfonate in the form of fine small needles with a melting point of 82-86° C.

EXAMPLE 8

3-Methoxy-8β-prop-1-(Z)-enyl-17β-(tetrahydropyran-2-yloxy)-estra-1,3,5(10)-triene A solution of 100 mg of 8β-formyl-3-methoxy-17β-(tetrahydropyran-2-yloxy)-estra-1,3,5(10)-triene in 5 ml of DMSO was mixed under argon first with 830 mg of ethyltriphenyl phosphonium bromide, then carefully with 64 mg of sodium hydride (80% in paraffin oil) and then heated slowly for 2 hours to an internal temperature of 60° C. After cooling, 10 ml of water was added in drops, extracted several times with ethyl acetate, the collected organic phases were washed with water and dried on magnesium sulfate. After the solvent was removed, the residue was purified by chromatography on silica gel (solvent mixture: cyclohexane/ethyl acetate=30/1). 24 mg (23%) of 8β-propenyl steroid in the form of a colorless foam was obtained.

8β-prop-1-(Z)-enyl-estra-1,3,5(10)-triene-3,17β-diol 24 mg of 3-methoxy-8β-(prop-1-(Z)-enyl)-17β-(tetrahydropyran-2-yloxy)-estra-1,3,5(10)-triene was reacted according to the general operating instructions for cleaving THP and 3-methyl ether. The crude 8β-prop-1-(Z)-enyl-estra-1,3,5(10)-triene-3,17β-diol was obtained after a purification on silica gel (solvent mixture: cyclohexane/ethyl acetate=7/3) in the form of colorless crystals with a melting point of 119-125° C. in a yield of 10 mg (66%).

EXAMPLE 9

3-methoxy-17α-ethinyl-8β-vinyl-estra-1,3,5(10)-trien-17β-ol

Under argon, 85 mg of 3-methoxy-8β-vinyl-estra-1,3,5(10)-trien-17-one in 8 ml of THF was dissolved, cooled to −78° C. and mixed with 5.5 ml of ethinylmagnesium bromide solution (0.5 M in THF) and 100 mg of lithium acetylide-ethylene diamine complex. While being heated to room temperature, the reaction mixture was stirred for 3 hours, then cooled to 0° C. and mixed with 10 ml of saturated ammonium chloride solution. The mixture was extracted several times with ethyl acetate, the collected organic phases were washed with saturated sodium chloride solution, dried on magnesium sulfate and concentrated by evaporation in a vacuum. By chromatography of the residue on silica gel (solvent mixture: cyclohexane/ethyl acetate=9:1), 30 mg (33%) of oily 17α-ethinyl-3-methoxy-8β-vinyl-estra-1,3,5(10)-trien-17β-ol was obtained.

17α-ethinyl-8β-vinyl-estra-1,3,5(10)-triene-3,17β-diol

A solution of 15 mg of 17α-ethinyl-3-methoxy-8β-vinyl-estra-1,3,5(10)-trien-17β-ol and 82 mg of tetrabutylammonium iodide in 2 ml of dichloromethane was cooled under argon to −78° C., mixed with 0.3 ml of a boron trichloride solution (1 M in dichloromethane) and stirred for 24 hours at 0° C. Then, the reaction solution was added in drops to a saturated ammonium chloride solution that was cooled to 5° C., the mixture was extracted several times with diethyl ether, the collected organic phases were washed with saturated sodium chloride solution, dried on magnesium sulfate and concentrated by evaporation in a vacuum. By chromatography of the residue on silica gel (solvent mixture: cyclohexane/ethyl acetate=7:3), 5 mg (35%) of 17α-ethinyl-8β-vinyl-estra-1,3,5(10)-triene-3,17β-diol was obtained with a melting point of 156° C.

EXAMPLE 10

3-methoxy-17α-methyl-8β-vinyl-estra-1,3,5(10)-triene-17β-diol

A solution of 50 mg of 3-methoxy-8β-vinyl-estra-1,3,5(10)-trien-17-one in 2 ml of anhydrous THF was added in drops under argon to a solution of 1 ml of methyllithium solution (1.6 M in diethyl ether) that was cooled to −78° C., then 0.5 ml of anhydrous dimethylformamide was added and stirred for 1.5 hours while being heated to room temperature. The mixture was mixed with saturated sodium bicarbonate solution, extracted several times with ethyl acetate, the collected organic phases were washed with water and dried on magnesium sulfate. By concentration by evaporation of the organic phases, 42 mg (80%) of crude 3-methoxy-17α-methyl-8β-vinyl-estra-1,3,5(10)-trien-17β-ol was obtained, which was used for cleaving 3-methyl ether without further purification.

17α-methyl-8β-vinyl-estra-1,3,5(10)-triene-3,17β-diol 40 mg of 3-methoxy-17α-methyl-8β-vinyl-estra-1,3,5(10)-trien-17β-ol was reacted according to the general operating instructions for cleaving 3-methyl ether. The thus obtained 17α-methyl-8β-vinyl-estra-1,3,5(10)-triene-3,17β-diol was obtained in a yield of 30 mg (78%) with a melting point of 129-130° C. after a purification on silica gel (solvent mixture: cyclohexane/ethyl acetate=7/3).

EXAMPLE 11

3-methoxy-8β-vinyl-estra-1,3,5(10)-triene-17α-(4'-nitro)-benzoate 0.48 ml of a 40% solution of diethylazodicarboxylate in toluene was added in drops to a mixture that consists of 100 mg of 3-methoxy-8β-vinyl-estra-1,3,5(10)-trien-17β-ol, 277 mg of triphenylphosphine, 175 mg of 4-nitrobenzoic acid and 5 ml of toluene, and it was stirred for 3 hours at 60° C. After cooling, it was extracted several times with ethyl acetate, the collected organic phases were washed in succession with saturated sodium bicarbonate solution and saturated sodium chloride solution, dried on magnesium sulfate and concentrated by evaporation in a vacuum. By chromatography on silica gel (solvent mixture: n-hexane/ethyl acetate=25/1), 84 mg (57%) of yellowish, oily 3-methoxy-8β-vinyl-estra-1,3,5(10)-triene-17α-(4'-nitro)-benzoate was obtained.

3-methoxy-8β-vinyl-estra-1,3,5(10)-trien-17α-ol

A solution of 80 mg of 3-methoxy-8β-vinyl-estra-1,3,5(10)-triene-17α-(4'-nitro)-benzoate in 12 ml of methanol and 0.4 ml of water was mixed with 480 mg of potassium carbonate and stirred for 24 hours at room temperature. Then, it was concentrated by evaporation in a vacuum to the greatest extent possible, the residue was taken up in water and extracted several times with ethyl acetate. The collected organic phases were washed with saturated sodium chloride solution, dried on magnesium sulfate and concentrated by evaporation in a rotary evaporator. In this way, 40 mg (54%) of 3-methoxy-8β-vinyl-estra-1,3,5(10)-trien-17α-ol was obtained.

8β-vinyl-estra-1,3,5(10)-trien-3,17α-ol 40 mg (0.13 mmol) of 3-methoxy-8β-vinyl-estra-1,3,5(10)-trien-17α-ol was reacted according to the general operating instructions for cleaving 3-methyl ether. The 8β-vinyl-estra-1,3,5(10)-triene-3,17α-diol that was obtained in this case was obtained in a yield of 9 mg (24%) with a melting point of 149-151° C. after a purification on silica gel (solvent mixture: cyclohexane/ethyl acetate=7/3).

EXAMPLE 12

16-dimethyl-3-methoxy-8β-vinyl-estra-1,3,5(10)-trien-17-one

A solution of 150 mg of 3-methoxy-8β-vinyl-estra-1,3,5(10)-trien-17β-ol in 6 ml of anhydrous THF that was cooled to −40° C. was mixed under argon with 1.2 ml of a solution of lithium diisopropylamide (2 M in THF/n-heptane/ethylbenzene) and stirred for 1 hour at this temperature. Then, 0.24 ml of methyl iodide was added at the same temperature and stirred for another hour while being heated to room temperature. Then, it was cooled to −5° C., 4 ml of 2N sodium hydroxide solution was added, and the mixture was extracted several times with ethyl acetate. The collected organic phases were washed with water, dried on $MgSO_4$ and concentrated by evaporation in a vacuum.

The crude product that was thus obtained was used again under the same reaction conditions.

130 mg (80%) of yellow-brown, oily 16-dimethyl-3-methoxy-8β-vinyl-estra-1,3,5(10)-trien-17-one was obtained as raw material.

16-dimethyl-8β-vinyl-estra-1,3,5(10)-trien-3,17β-ol 130 mg of crude 16-dimethyl-3-methoxy-8β-vinyl-estra-1,3,5(10)-trien-17-one was reacted according to the general operating instructions for cleaving 3-methyl ether. The crude product that was obtained was purified by chromatography on silica gel (solvent mixture: cyclohexane/ethyl acetate=85/15). In this case, 50 mg (40%) of colorless, crystalline 16-dimethyl-8β-vinyl-estra-1,3,5(10)-trien-3,17β-ol with a melting point of 113-123° C. (decomposition) accumulated.

EXAMPLE 13

3-methoxy-8β-(prop-1-(E)-enyl)-17β-(tetrahydropyran-2-yloxy)-estra-1,3,5(10)-triene A mixture that consists of 4 ml of pentane, 20 ml of 1,2-dimethoxyethane and 2 ml of diethylethylphosphonate that was cooled to −78° C. was mixed under argon with 8 ml of a 1.7 M solution of tert-butyllithium (in pentane) and stirred for 15 minutes at this temperature. Then, a solution that consists of 500 mg of 8β-formyl-3-methoxy-17β-(tetrahydropyran-2-yloxy)-estra-1,3,5(10)-triene in 8 ml of 1,2-dimethoxyethane and 1.5 ml of pentane was added in drops, stirred for 30 minutes while being exposed to continuous cooling and stirred for 1.5 hours while being heated to room temperature. Then, the pentane was distilled off, and the remaining reaction solution was refluxed for 3 hours.

The mixture was poured onto crushed ice, and the fine white precipitate was filtered off and dried. After a chromatographic purification on silica gel (solvent mixture: cyclohexane/ethyl acetate=20/1), 275 mg (54%) of 3-methoxy-8β-(prop-1-(E)-enyl)-17β-(tetrahydropyran-2-yloxy)-estra-1,3,5(10)-triene in the form of a colorless foam was obtained.

8β-prop-1-(E)-enyl-estra-1,3,5(10)-triene-3,17β-diol 275 mg of 3-methoxy-8β-(prop-1-(E)-enyl)-17β-(tetrahydropyran-2-yloxy)-estra-1,3,5(10)-triene was reacted according to the general operating instructions for cleaving THP and 3-methyl ether. The crude 8β-prop-1-(E)-enyl-estra-1,3,5(10)-triene-3,17β-diol was obtained in a yield of 108 mg (52%) after apurification on silica gel (solvent mixture: cyclohexane/ethyl acetate=8/2) with a melting point of 110-125° C.

EXAMPLE 14

3-methoxy-17α-trifluoromethyl-17β-trimethylsilyloxy-8β-vinyl-estra-1,3,5(10)-triene A solution of 80 mg of 3-methoxy-8β-vinyl-estra-1,3,5 (10)-trien-17-one in 2 ml of THF that was cooled to 0° C. was mixed under argon with 0.2 ml of trifluoromethyltrimethyl-silane, and 5 mg of tetrabutylammonium fluoride trihydrate, and it was stirred for 24 hours at room temperature. The dark reaction solution was poured onto ice-cold water, extracted several times with ethyl acetate, washed with saturated sodium chloride solution, dried on magnesium sulfate and concentrated by evaporation in a vacuum. The crude product that was obtained was purified by flash chromatography on silica gel (solvent mixture: cyclohexane/ethyl acetate=9/1). 63 mg (54%) of 3-methoxy-17α-trifluoromethyl-17β-trimethylsilyloxy-8β-vinyl-estra-1,3,5(10)-triene was obtained as a dark oil.

17α-Trifluoromethyl-8β-vinyl-estra-1,3,5(10)-triene-3,17β-diol 1.26 g of tetrabutylammonium fluoride trihydrate was added to a solution of 60 mg of 3-methoxy-17α-trifluoromethyl-17β-trimethylsilyloxy-8β-vinyl-estra-1,3,5(10)-triene in 6 ml of THF, and it was stirred for 2 hours at room temperature. Then, saturated sodium chloride solution was added, it was extracted several times with ethyl acetate, the collected organic phases were dried on magnesium sulfate and concentrated by evaporation in a vacuum. The oily, yellow residue (50 mg) was used in the next stage without further purification.

A solution of 50 mg of crude 3-methoxy-17α-trifluoromethyl-8β-vinyl-estra-1,3,5(10)-trien-17β-ol in 3 ml of dichloromethane that was cooled to −78° C. was mixed under argon in succession with 243 mg of tetrabutylammonium iodide and 0.7 ml of a 1 M boron trichloride solution in dichloromethane and stirred for 2 hours while being heated to 0° C. Then, the reaction mixture was added in drops to a 5° C. saturated ammonium chloride solution and extracted several times with ethyl acetate. The collected organic phases were washed with saturated sodium chloride solution, dried on magnesium sulfate and concentrated by evaporation in a vacuum. The crude product (90 mg) was purified by chromatography on silica gel (solvent mixture: cyclohexane/ethyl acetate=7/3). 25 mg (52%) of powdery 17α-trifluoromethyl-8β-vinyl-estra-1,3,5(10)-triene-3,17β-diol with a melting point of 76-79° C. was obtained.

EXAMPLE 15

2-fluoro-3,17β-bis-(tetrahydropyran-2-yloxy)-8β-vinyl-estra-1,3,5(10)-triene 3 ml of a 1.3 M s-butyllithium solution was added in drops under argon to a solution of 120 mg of 3,17β-bis-(tetrahydropyran-2-yloxy)-8β-vinyl-estra-1,3,5(10)-triene in 4 ml of THF that was cooled to −78° C., it was stirred for 30 minutes and then a solution that consists of 650 mg of N-fluorodibenzenesulfonimide in 4 ml of THF was added in drops while being exposed to continuous cooling. The reaction mixture was stirred first for 1 hour at −78° C. then for another 16 hours while being heated to room temperature. The reaction solution was poured onto ice water, extracted several times with ethyl acetate, the collected organic phases were washed with saturated sodium chloride solution, dried on magnesium sulfate and concentrated by evaporation in a vacuum. The dark, oily crude product (330 mg) was used in the next stage without further purification.

2-fluoro-8β-vinyl-estra-1,3,5(10)-triene-3,17β-diol

The oily crude product of the last stage was dissolved in 10 ml of methanol, mixed with 1 ml of water and 250 mg of oxalic acid dihydrate and heated for 1 hour to 60° C.

For working-up, it was diluted with ethyl acetate, washed in succession with saturated sodium bicarbonate solution and saturated sodium chloride solution, dried on magnesium sulfate and concentrated by evaporation in a vacuum. The crude product that was obtained was separated by chromatography on silica gel (solvent mixture: cyclohexane/ethyl acetate=8/2). The 2fluoro-8β-vinyl-estra-1,3,5(10)-triene-3,17β-diol that was thus obtained (15 mg, 18%) had a melting point of 67-73° C.

EXAMPLE 16

3,17β-bis-(tetrahydropyran-2-yloxy)-8β-vinyl-estra-1,3,5(10)-trien-2-ol 3 ml of a 1.3 M s-butyllithium solution was added in drops under argon to a solution of 120 mg of 3,17β-bis-(tetrahydropyran-2-yloxy)-8β-vinyl-estra-1,3,5(10)-triene in 4 ml of THF that was cooled to −78° C., it was stirred for 30 minutes and then 0.5 ml of trimethyl borate was added in one shot. While being heated to 0° C., it was stirred for 2 hours, then 2 ml of 3N sodium hydroxide solution and 1 ml of 30% hydrogen peroxide were added and finally stirred for another 4 hours at room temperature.

The mixture was diluted with water, saturated sodium hydrogen sulfite solution was added, extracted several times with methyl-tert-butyl ether, the collected organic phases were washed with saturated sodium chloride solution, dried on magnesium sulfate and concentrated by evaporation in a vacuum. By chromatography of the evaporation residue on silica gel (solvent mixture: n-hexane/ethyl acetate=9:1), 65 mg (52%) of colorless, oily 3,17β-bis-(tetrahydropyran-2-yloxy)-8β-vinyl-estra-1,3,5(10)-trien-2-ol was obtained.

8β-vinyl-estra-1,3,5(10)-triene-2,3,17β-triol

The oily product of the last stage was dissolved in 3 ml of methanol, mixed with 0.3 ml of water and 50 mg of oxalic acid dihydrate and heated for 1 hour to 60° C.

For working-up, it was diluted with ethyl acetate, washed in succession with saturated sodium bicarbonate solution and saturated sodium chloride solution, dried on magnesium sulfate and concentrated by evaporation in a vacuum. The yellowish, powdery 8β-vinyl-estra-1,3,5(10)-triene-2,3,17β-triol that was thus obtained (38 mg, 95%) had a melting point of 82-85° C. (decomposition).

General Operating Instructions for Cleaving Ether of 3-Methoxy-17-(tetrahydropyran-2-yloxy)-estratrienes and -tetraenes into the Corresponding 17-alcohols by Acid 1.0 mmol of steroid is dissolved in 22 ml of acetone and stirred with 1.5 ml of 4N hydrochloric acid for 3 hours at room temperature. If, during this time, conversion is not completed, the solution is additionally heated for 1.5 hours to 50° C. Then, it is diluted with 20 ml of water, extracted several times with dichloromethane, the collected organic phases are dried with magnesium sulfate, and the solvent is distilled off in a rotary evaporator. The crude 17-hydroxyl compounds that are produced in this way accumulate as foams and are immediately further processed.

General Operating Instructions for Cleaving Ether of 3-methoxy-17-(tetrahydropyran-2-yloxy)-estratrienes and -tetraenes into the Corresponding 3,17-diols with Acid and DIBAH 1.0 mmol of steroid is dissolved in 15-20 ml of anhydrous toluene, cooled to 0° C. and mixed carefully with 3.0 ml of DIBAH under argon. The reaction mixture is slowly refluxed and kept at this temperature for 3.5 hours. Then, in succession, 10 ml of ethanol, 10 ml of ethanol-water mixture (v/v:=1/1) and 10 ml of semi-concentrated hydrochloric acid are carefully added in drops to the solution that is cooled to 0° C., and it is extracted several times with ethyl acetate. The collected organic phases are washed neutral with water, dried with magnesium sulfate and evaporated to the dry state in a rotary evaporator. The yields lie between 90 and 99%.

BRIEF DESCRIPTION OF DRAWING:

FIG. 3: A third general synthesis route for the examples.

Figure 1:
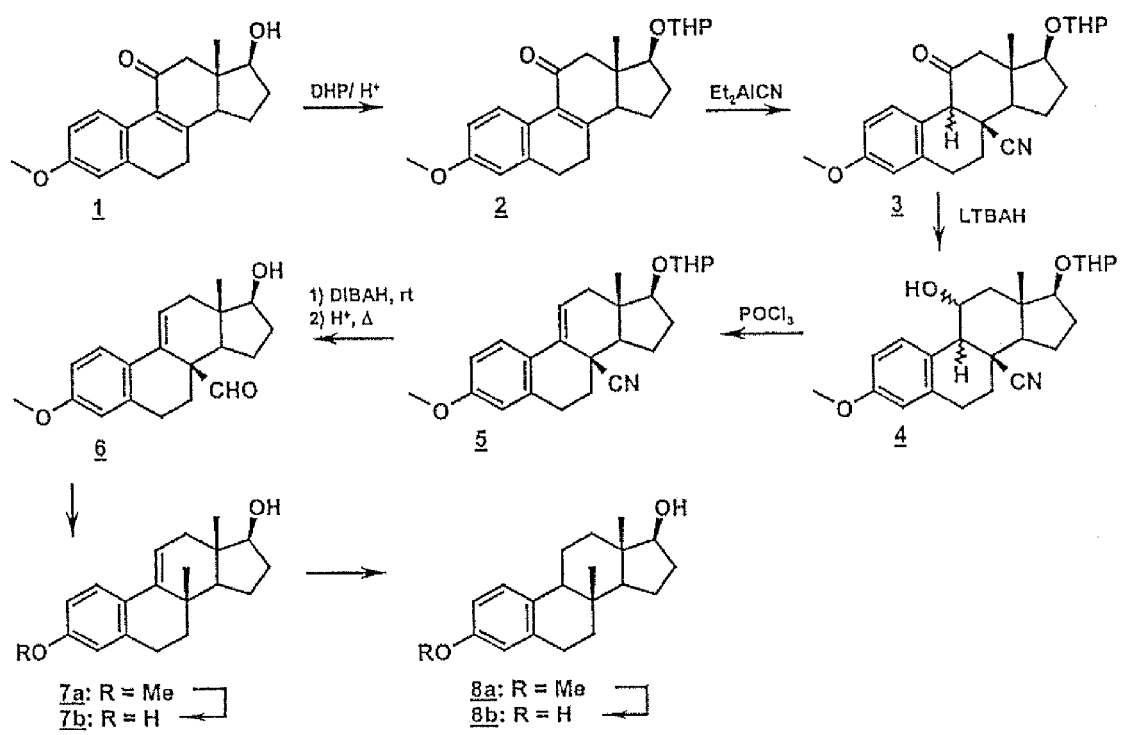
FIG. 1: A general synthesis route for the examples.
Figure 2:
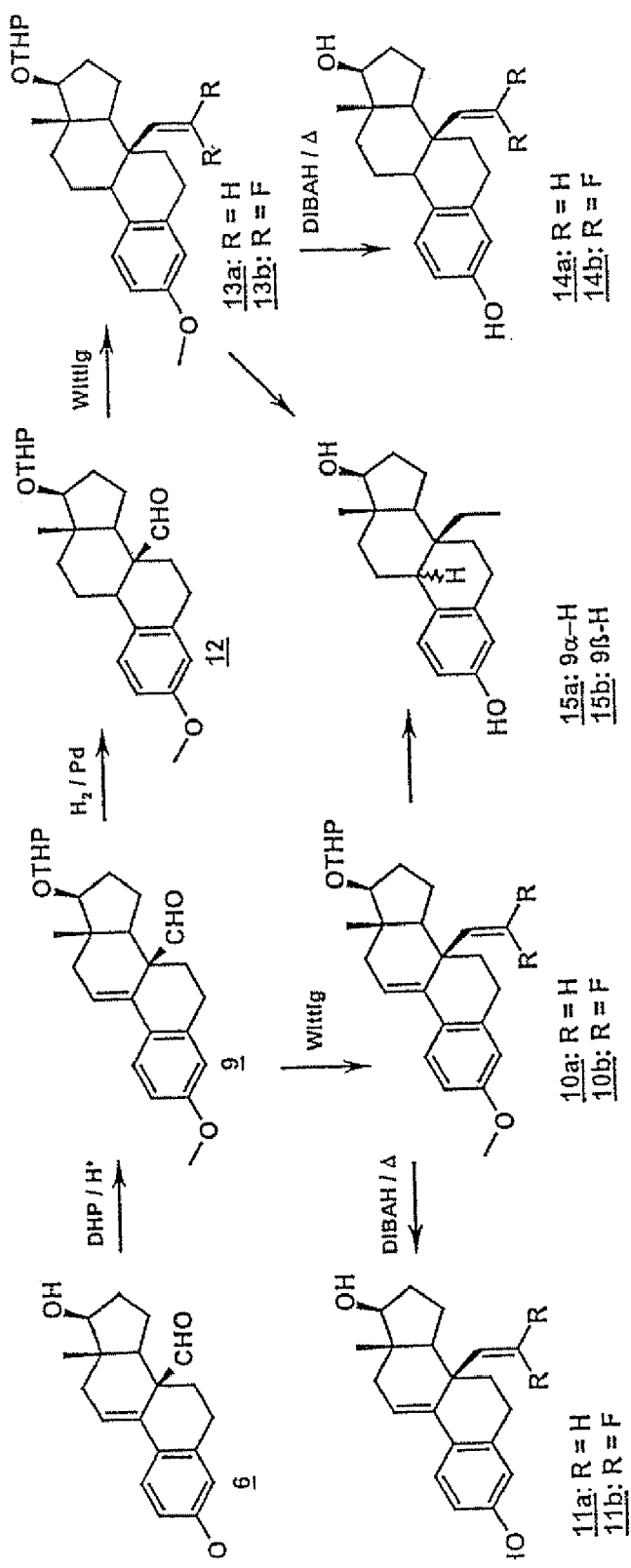
FIG. 2: A second general synthesis route for the examples.

The invention claimed is:
1. A 8β-Substituted estra-1,3,5(10)-triene compound of formula I

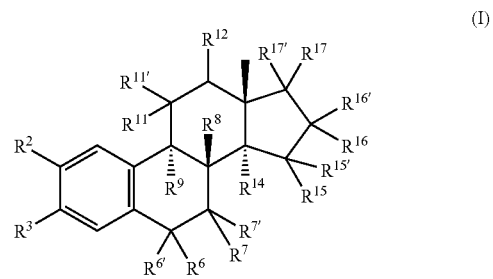

(I)

in which
R$^2$ means a hydrogen atom, a halogen atom:
a radical R$^{18}$— or R$^{18}$—O—, in which R$^{18}$ means a hydrogen atom or a straight-chain or branched-chain, saturated or unsaturated hydrocarbon radical with up to 6 carbon atoms, or a trifluoromethyl group;
a group R$^{19}$ SO$_2$—O—, in which R$^{19}$ is an R$^{20}$R$^{21}$N group, in which R$^{20}$ and R$^{21}$, independently of one another, mean a hydrogen atom, a C$_1$-C$_5$-alkyl radical, a group C(O)R$^{22}$, in which R$^{22}$ represents an optionally substitued, straight-chain or branched-chain, saturated or unsaturated in up to three places, an optionally partially or completely halogenated hydrocarbon radical with up to 10 carbon atoms, an optionally substituted C$_3$-C$_7$-cycloalkyl radical, an optionally substituted C$_4$-C$_{15}$-cycloalkalkyl radical or an optionally substituted aryl, heteroayl or aralkyl radical, or R$^{20}$R$^{21}$N means a polymethylenimino radical with 4 to 6 C atoms or a morpholino radical;
R$^3$ means a group R$^{18'}$—O—, R$^{19}$SO$_2$—O— or —O—C(O)R$^{22}$, in which R$^{18'}$ is a hydrogen atom or a straight-chain or branched-chain, saturated or unsaturated hydrocarbon radical with up to 6 carbon atoms, a trifluoromethyl group, or an aryl, heteraryl or aralkyl radical;

$R^6$ and $R^7$ each mean a hydrogen atom or together an additional bond;

$R^{6'}$ and $R^{7'}$, are each independently a hydrogen atom, a halogen atom, a group $R^{18}$—O—, $R^{19}SO_2$—O— or —$R^{22}$;

$R^8$ means a branched-chain, optionally partially or completely halogenated alkyl radical with up to 5 carbon atoms, or a straight chain or branched chain, optionally partially or completely halogenated alkenyl radical with up to 5 carbon atoms, an ethinyl or prop-1-inyl radical;

$R^9$ means a hyrogen atom, a straight-chain or branched-chain, saturated or unsaturated hydrocarbon radical with up to 5 carbon atoms, or together with $R^{11}$ means an additional bond;

$R^{11}$ means a hydrogen atom or together with $R^9$ or together with $R^{12}$ means an additional bond;

$R^{11'}$ means a hydrogen atom, a halogen atom, a saturated or unsaturated, optionally partially or completely halogenated (F, Cl) hydrocarbon radical, which has a maximum linear chain length of 4 carbon atoms, or a group —X—$R^{18''}$, in which X is an oxygen or sulfur atom, and $R^{18''}$ is an alkyl radical with 1 to 3 carbon atoms;

$R^{12}$ means a hydrogen atom or together with $R^{11}$ means an additional bond;

$R^{14}$ means a hydrogen atom or together with $R^{15}$ means an additional bond;

$R^{15}$ means a hydrogen atom or together with $R^{14}$ or togehter with $R^{16}$ means an additional bond;

$R^{16}$ means a hydrogen atom or together with $R^{15}$ means an additional bond;

$R^{15'}$ and $R^{16'}$, independently of one another, mean a hydrogen atom, a halogen atom, a group $R^{18}$—O—, $R^{19}SO_2$—O— or —$R^{22}$;

$R^{17}$ and $R^{17'}$ each mean a hydrogen atom; a hydrogne atom and a halogen atom; a hydrogen atom and a benzyloxy group; a hydrogen atom and a group $R^{19}SO_2$—O—; a group $R^{18}$ and a group —C(O)$R^{22}$ or —O—C(O)$R^{22}$; a group $R^{18}$—O— and $R^{18}$—; a group $R^{18}$—O— and a group —O—C(O)$R^{22}$; or $R^{17}$ and $R^{17'}$ togehter mean a group =$CR^{23}R^{24}$, in which $R^{23}$ and $R^{24}$, independently of one another, represent a hydrogen atom and a halogen atom, or together an oxygen atom;

excluding the compounds of formula I, in which $R^3$ is a hydroxy, methoxy or acetyloxy group, and simultaneously $R^2$ represents a hydrogen atom, $R^6$, $R^{6'}$, $R^7$ and $R^{7'}$ in each case represent a hydrogen atom;

$R^9$ represents a hydrogen atom or $R^9$ and $R^{11}$ together represent an additional bond, $R^{11'}$ and $R^{12}$ in each case represent a hydrogen atom, $R^{14}$, $R^{15}$, $R^{15'}$, $R^{16}$ and $R^{16'}$ in each case represent a hydrogen atom, and $R^{17}$ and $R^{17'}$ form a β-hydroxy group and a hydrogen atom; form a β-(2-bromoacetyl)oxy group and hydrogen atom; or form a β-acetyl group and a hydrogen atom; or $R^{17}$ and $R^{17'}$ together represent an oxygen atom.

2. A compound of formula I according to claim 1, in which $R^2$ means a hydrogen or halogen atom or a hydroxy groups;

$R^3$ means a group $R^{18}$—O—, $R^{19}SO_2$—O— or —O—C(O)$R^{22}$, $R^6$ and $R^7$ each mean hydrogen atom;

$R^{6'}$ means a hydrogen atom, or a hydroxy group, a group $R^{22}$;

$R^{7'}$ means a hydrogen atom, a halogen atom, a group $R^{18}$—O—, $R^{19}SO_2$—O— or —$R^{22}$;

$R^8$ means a branched-chain, optically partially or completely halogenated alkyl radical with up to 5 carbon atoms, or a straight chain or branched chain, optionally partially or completely halogenated alkenyl radical with up to 5 carbon atoms, an ethinyl or prop-1-inyl radical;

$R^9$ means a hydrogen atom or together with $R^{11}$ an additional bond;

$R^{11}$ means a hydrogen atom or together with $R^9$ an additional bond;

$R^{11'}$ means a hydrogen atom, a halogen atom, a saturated or unsaturated, optionally partially or completely halogenated (F, Cl) hydrocarbon radical, which has a maximum linear chain length of 4 carbon atoms, or group —X—$R^{18''}$, in which X is a sulfur atom, and $R^{18''}$ is an alkyl radical with 1 to 3 carbon atoms;

$R^{12}$, $R^{14}$, $R^{15}$ in each case mean a hydrogen atom;

$R^{16'}$ means a hydrogen atom, a halogen atom, a group $R^{18}$—O—, $R^{19}SO_2$—O— or —$R^{22}$;

$R^{17}$ and $R^{17'}$ in each case mean a hydrogen atom, a hydrogen atom and a halogen atom; a hydrogen atom and a benzyloxy group; a hydrogen atom and a group $R^{19}SO_2$—O—; a group $R^{18}$ and a group —C(O)$R^{22}$ or —O—C(O)$R^{22}$; a group $R^{18}$—O— and a group $R^{18}$—; a group $R^{18}$—O— and a group —O—C(O)$R^{22}$; or $R^{17}$ and $R^{17'}$ together mean a group =$CR^{23}R^{24}$, in which $R^{23}$ and $R^{24}$, independently of one another, represent a hydrogen atom and a halogenatom, or together an oxygen atom.

3. A compound of formula I according to claim 1, in which $R^2$ means a hydrogen atom or a fluorine atom or a hydroxy group, $R^3$ means a group $R^{18'}$—O—, $R^{19}SO_2$—O— or —O—C(O)$R^{22}$ $R^6$ and $R^7$ in each case mean a hydrogen atom;

$R^{6'}$ means a hydrogen atom or a hydroxy group, $R^{7'}$ means a hydrogen atom, a fluorine or chlorine atom, a group $R^{18}$—O—, $R^{19}SO_2$—O— or —$R^{22}$, $R^{18}$ means a hydrogen atom or a straight-chain or branched-chain, saturated or unsaturated hydrocarbon radical with up to 6 carbon atoms, or a trifluoromethyl group;

$R^{19}$ is an $R^{20}R^{21}N$ group, $R^{20}$ and $R^{21}$, independently of one another, mean a hydrogen atom, a $C_1$-$C_5$-alkyl radical, a group C(O)$R^{22}$, $R^{22}$ represents an optionally substituted, straight-chain or branched-chain, saturated or unsaturated in up to three places, an optionally partially or completely halogenated hydrocarbon radical with up to 10 carbon atoms, an optionally substituted $C_3$-$C_7$-cycloalkyl radical, an optionally substituted $C_4$-$C_{15}$-cycloalkylalkyl radical or an optionally substituted aryl, heteroaryl or aralkyl radical, or $R^{20}R^{21}N$ means a polymethylenimino radical with 4 to 6 C atoms or a morpholino radical;

$R^9$ means a hydrogen atom or together with $R^{11}$ an additional bond;

$R^{11'}$ means a hydrogen atom, a fluorine or chlorine atom, a saturated, straight-chain or branched-chain $C_1$-$C_4$-alkyl group, a group —X—$R^{18''}$, in which X is a sulfur atom and R$^{18''}$ means a saturated, straight-chain or branched-chain C$_1$-C$_3$-alkyl group, a chloromethyl or chloroethyl group;

R$^{12}$, R$^{14}$, R$^{15}$ and R$^{16}$ in each case mean a hydrogen atom;

R$^{16'}$ means a hydrogen atom, a fluorine or chlorine atom or a group R$^{18}$—O— or —R$^{22}$;

R$^{17}$ and R$^{17'}$ in each case mean a hydrogen atom; a hydrogen atom and a halogen atom; a hydrogen atom and a benzyloxy group; a hydrogen atom and a group R$^{19}$SO$_2$—O—; a group R$^{18}$ and a group —C(O)R or —O—C(O)R$^{22}$; a group R$^{18}$—O— and a group R$^{18}$—; a group R$^{18}$—O— and a group —O—C(O)R$^{22}$; or R$^{17}$ and R$^{17'}$ together mean a group =CR$^{23}$R$^{24}$, in which R$^{23}$ and R$^{24}$, independently of one another, represent a hydrogen atom and a halogen atom, or together an oxygen atom.

4. A compound of formula I according to claim 1, in which
R$^{6'}$, R$^{7'}$, R$^9$, R$^{11}$, R$^{14}$, R$^{15}$, R$^{15'}$ and R$^{16}$ in each case stand for a hydrogen atom or R$^{6'}$, R$^{7'}$, R$^{14}$, R$^{15}$, R$^{15'}$ and R$^{16}$ in each case stand for a hydrogen atom and R$^9$ and R$^{11}$ together stand for an additional bond, and all other substituents have the meanings that are indicated in claim 1.

5. A compound of formula I according to claim 1, which have a double bond in position 9(11), 14(15) or 15(16) or two double bonds in positions 9(11) and 14(15) or 15(16).

6. A compound of general formula I according to claim 1, in which
R$^{17}$ and R$^{17'}$ are a group R$^{18}$—O— and a group R$^{18}$—; a group R$^{18}$— and a group —O—C(O)R$^{22}$.

7. A compound of formula I according to claim 6, in which
R$^{17}$ and R$^{17'}$ are a hydroxy group and a hydrogen atom, a C$_1$-C$_4$-alkyl group or C$_2$-C$_4$-alkinyl group.

8. A compound of formula I according to claim 7, in which
R$^{17}$ and R$^{17'}$ are a hydroxy group and a hydrogen atom, a methyl, ethinyl, or prop-1-inyl group.

9. A compound of formula I according to claim 1, in which
R$^{16'}$ stands for a group R$^{18}$—O— or R$^{19}$SO$_2$—O—, and R$^{17}$ and R$^{17'}$ each stand for a hydrogen atom.

10. A compound of formula I according to claim 1, which is
8β-Vinyl-estra-1,3,5(10),9(11)-tetraene-3,17β-diol
3-methoxy-8β-vinyl-estra-1,3,5(10),9(11)-tetraen-17β-ol
8β-(2',2'-difluorovinyl)-estra-1,3,5(10),9(11)-tetraene-3,17β-diol
8-(2',2'-difluorovinyl)-3-methoxy-estra-1,3,5(10),9(11)-tetraen-17β-ol
8β-vinyl-estra-1,3,5(10)-triene-3,17β-diol
3-methoxy-8β-vinyl-estra-1,3,5(10)-trien-17β-ol
8β-(2',2'-difluorovinyl)-estra-1,3,5(10)-triene-3,17β-diol
8β-(2',2'-difluorovinyl)-3-methoxy-estra-1,3,5(10)-trien-17β-ol
8β-vinyl-estradiol-3-sulfamate
8β-vinyl-estradiol-3,17-disulfamate
8β-vinyl-estradiol-3-(N-acetyl)-sulfamate
8β-vinyl-estrone-3-sulfamate
8β-vinyl-estron-3-acetate
8β-vinyl-estriol
8β-vinyl-estriol-3-sulfamate
8β-(prop-(Z)-enyl)-estradiol
8β-ethinyl-estradiol
17α-ethinyl-8β-vinyl-estra-1,3,5(10)-triene-3,17β-diol
17α-methyl-8β-vinyl-estra-1,3,5,(10)-triene-3,17β-diol
8β-vinyl-estra-1,3,5(10)-triene-3,17α-diol
8β-vinyl-estradiol-diacetate
8β-vinyl-estradiol-17-valerianate or
17β-acetoxy-8β-vinyl-estra-1,3,5(10)-trien-3-ol.

11. A method for
in-vitro treatment of male infertility;
in-vivo treatment of male infertility;
in-vitro treatment of female infertility;
in-vivo treatment of female infertility;
hormone replacement therapy in a patient in need of replacement of estrogen;
therapy of osteoporosis; treatment of arteriosclerosis: or treatment of benign prostate hyperplasia;
comprising administering to a subject in need thereof an effective amount of an 8β-substituted estra-1,3,5(10)-triene compound of formula I'

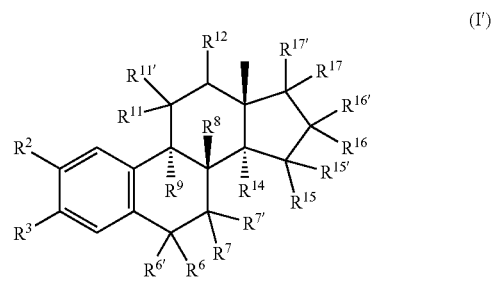

in which
R$^2$ means a hydrogen atom, a halogen atom;
a radical R$^{18}$— or R$^{18}$—O—, in which R$^{18}$ means a hydrogen atom or a straight-chain or branched-chain, saturated or unsaturated hydrocarbon radical with up to 6 carbon atoms or, a trifluoromethyl group;
a group R$^{19}$SO$_2$—O—, in which R$^{19}$ is an R$^{20}$R$^{21}$N, in which R$^{20}$ and R$^{21}$, independently of one another, mean a hydrogen atom, a C$_1$-C$_5$-alkyl radical, a group C(O)R$^{22}$, in which R$^{22}$ represents an optionally substituted, straight-chain or branched-chain, saturated or unsaturated in up to three places, an optionally partially or completely halogenated hydrocarbon radical with up to 10 carbon atoms, an optionally substituted C$_3$-C$_7$-cycloalkyl radical, an optionally substituted C$_4$-C$_{15}$-cycloalkylalkyl radical or an optionally substituted aryl, heteroaryl or aralkyl radical, or R$^{20}$R$^{21}$N means a polymethylenimino radical with 4 to 6 C atoms or a morpholino radical;
R$^3$ means a group R$^{18'}$—O—, R$^{19}$SO$_2$—O— or —O—C(O)R$^{22}$, in which R$^{18'}$ is a atom or a straight-chain or branched-chain, saturated or unsaturated hydrocarbon radical with up to 6 carbon atoms, a trifluoromethyl group, or an aryl heteroaryl or aralkyl radical;
R$^6$ and R$^7$ each mean a hydrogen atom or together an additional bond;
R$^{6'}$ and R$^{7'}$, are each independently a hydrogen atom, a halogen atom, a group R$^{18}$—O—, R$^{19}$SO$_2$—O— or —R$^{22}$;
R$^8$ means a branched-chain, optionally partially or completely halogenated alkyl radical with up to 5 carbon atoms, or a straight chain or branched chain, optionally partially or completely halogenated alkenyl radical with up to 5 carbon atoms, an $R^9$ means a hydrogen atom, a straight-chain or branched-chain, saturated or unsaturated hydrocarbon radical with up to 5 carbon atoms, or together with $R^{11}$ means an additional bond;

$R^{11}$ means a hydrogen atom or together with $R^9$ or together with $R^{12}$ means an additional bond;

$R^{11'}$ means a hydrogen atom, a halogen atom, a saturated or unsaturated, optionally partially or completely halogenated (F, Cl) hydrocarbon radical, which has a maximum linear chain length of 4 carbon atoms, or a group —X—$R^{18''}$, in which X is an oxygen or sulfur atom, and $R^{18''}$ is an alkyl radical with 1 to 3 carbon atoms;

$R^{12}$ means a hydrogen atom or together with $R^{11}$ means an additional bond;

$R^{14}$ means a hydrogen atom or together with $R^{15}$ means an additional bond;

$R^{15}$ means a hydrogen atom or together with $R^{14}$ or together with $R^{16}$ means an additional bond;

$R^{16}$ means a hydrogen atom or together with $R^{15}$ means an additional bond;

$R^{15'}$ and $R^{16'}$, independently of one another, mean a hydrogen atom, a halogen atom, a group $R^{18}$—O—, $R^{19}SO_2$—O— or —$R^{22}$;

$R^{17}$ and $R^{17'}$ each mean a hydrogen atom and a halogen atom; a hydrogen atom and a benzyloxy group; a hydrogen atom and a group $R^{19}SO_2$—O—; a group $R^{18}$ and a group —C(O)$R^{22}$ or —O—C(O)$R^{22}$; a group $R^{18}$—O— and a group $R^{18}$—; a group $R^{18}$—O— and a group —O—C(O)$R^{22}$; or $R^{17}$ and $R^{17'}$ together mean a group =$CR^{23}R^{24}$, in which $R^{23}$ and $R^{24}$, independently of one another, represent a hydrogen atom and a halogen atom, or together an oxygen atom, wherein said administration of the compound of formula I' achieves a selective effect on estrogen receptor beta.

12. A method according to claim 11, in which $R^2$ means a hydrogen or halogen atom or a hydroxy group;
$R^3$ means a group $R^{18'}$—O—, $R^{19}SO_2$—O— or —O—C(O)$R^{22}$;
$R^6$ and $R^7$ each mean a hydrogen atom;
$R^{6'}$ means a hydrogen atom, a hydroxy group, or a group $R^{22}$;
$R^{7'}$ means a hydrogen atom, a halogen atom, a group $R^{18}$—O—, $R^{19}SO_2$—O— or —$R^{22}$;
$R^8$ means a branched-chain, optionally partially or completely halogenated alkyl radical with up to 5 carbon atoms, or a straight chain or branched chain, optionally partially or completely halogenated alkenyl radical with up to 5 carbon atoms, an ethinyl or prop-1-inyl radical;
$R^9$ means a hydrogen atom or together with $R^{11}$ an additional bond;
$R^{11}$ means a hydrogen atom or together with $R^9$ an additional bond;
$R^{11'}$ means a hydrogen atom, a halogen atom, a saturated or unsaturated, optionally partially or completely halogenated (F, Cl) hydrocarbon radical, which has a maximum linear chain length of 4 carbon atoms, or a group —X—$R^{18''}$, in which X is a sulfur atom, and $R^{18''}$ is an alkyl radical with 1 to 3 carbon atoms;
$R^{12}$, $R^{14}$, $R^{15}$ and $R^{16}$ in each case mean a hydrogen atom;
$R^{16'}$ means a hydrogen atom, a halogen atom, a group $R^{18}$—O—, $R^{19}SO_2$—O— or —$R^{22}$;
$R^{17}$ and $R^{17'}$ in each case mean a hydrogen atom; a hydrogen atom and a halogen atom; a hydrogen atom and a benzyloxy group; a hydrogen atom and a group $R^{19}SO_2$—O—; a group $R^{18}$ and a group —C(O)$R^{22}$ or —O—C(O)$R^{22}$; a group $R^{18}$—O— and a group $R^{18}$—; a group $R^{18}$—O— and a group —O—C(O)$R^{22}$; or $R^{17}$ and $R^{17'}$ together mean a group =$CR^{23}R^{24}$, in which $R^{23}$ and $R^{24}$, independently of one another, represent a hydrogen atom and a halogen atom, or together an oxygen atom.

13. A method according to claim 11, in which $R^2$ means a hydrogne atom or a fluorine atom or a hydroxy group,
$R^3$ means a group $R^{18'}$—O—, $R^{19}SO_2$—O— or —O—C(O)$R^{22}$,;
$R^6$ and $R^7$ in each case mean a hydrogen atom;
$R^{6'}$ means a hydrogen atom or a hydroxy group,
$R^{7'}$ means a hydrogen atom, a fluorine or chlorine atom, a group $R^{18}$—O—, $R^{19}SO_2$—O— or —$R^{22}$;
$R^{18}$ means a hydrogen atom or a straight-chain or branched-chain, saturated or unsaturated hydrocarbon radical with up to 6 carbon atoms, or a trifluoromethyl group;
$R^{19}$ is an $R^{20}R^{21}N$ group,
$R^{20}$ and $R^{21}$, independently of one another, mean a hydrogen atom, a $C_1$-$C_5$-alkyl radical, a group $C(O)R^{22}$,
$R^{22}$ represents an optionally substituted, straight-chain or branched-chain, saturated or unsaturated in up to three places, an optionally partially or completely halogenated hydrocarbon radical with up to 10 carbon atoms, an optionally substituted $C_3C_7$-cycloalkyl radical, an optionally substituted $C_4$-$C_{15}$-cycloalkylalkyl radical or an optionally substituted aryl, heteraryl or aralkyl radical,
or $R^{20}R^{21}N$ means a polymethylenimino radical with 4 to 6 C atoms or a morpholino radical;
$R^8$ means a branched-chain, optionally partially or completely halogenated alkyl radical with up to 5 carbon atoms or a straight chain or branched chain, optionally partially or completely halogenated alkenyl radical with up to 5 carbon atoms, an ethinyl or pro-1-inyl radical;
$R^9$ means a hydrogen atom or together with $R^{11}$ an additional bond;
$R^{11'}$ means a hydrogen atom, a fluorine or chlorine atom, a saturated, straight-chain or branched-chain $C_1$-$C_4$-alkyl group, a group —X—$R^{18''}$, in which X is a sulfur atom and $R^{18''}$ means a saturated, straight-chain or branched-chain $C_1$-$C_3$alkyl group, a chloromethyl or chloroethyl group;
$R^{12}$, $R^{14}$, $R^{15}$ and $R^{16}$ in each case mean a hydrogen atom;
$R^{16'}$ means a hydrogen atom, a fluorine or chlorine atom or a group $R^{18}$—O or —$R^{22}$;
$R^{17}$ and $R^{17'}$ in each case mean a hydrogen atom; a hydrogen atom and a halogen atom; a hydrogen atom and a benzyloxy group; a hydrogen atom and a group $R^{19}SO_2$—O—; a group $R^{18}$ and a group —OC(O)$R^{22}$ or —O—C(O)$R^{22}$; a group $R^{18}$—O— and a group $R^{18}$—; a group $R^{18}$—O— and a group —O—C(O)$R^{22}$, in all above cases with $R^{18}$, $R^{19}$ and $R^{22}$ in each case in the meaning that is indicated under $R^2$ in claim 11; or $R^{17}$ and $R^{17'}$ together mean a group =$CR^{23}R^{24}$, in which $R^{23}$ and $R^{24}$, independently of one another, represent a hydrogen atom and a halogen atom, or together an oxygen atom.

14. A method according to claim 11, in which $R^{6'}$, $R^{7'}$, $R^9$, $R^{11}$, $R^{14}$, $R^{15}$, $R^{15'}$ and $R^{16}$ in each case stand for a hydrogen atom or $R^{6'}$, $R^{7'}$, $R^{14}$, $R^{15}$, $R^{15'}$ and $R^{16}$ in each case stand for a hydrogen atom and $R^9$ and $R^{11}$ together stand for an additional bond.

15. A method according to claim 11, wherein the estratrienes have a double bond in position 9(11), 14(15) or 15(16) or two double bonds in positions 9(11) and 14(15) or 15(16).

16. A method according to claim 11, in which $R^{17}$ and $R^{17'}$ are a group $R^{18}$—O— and a group $R^{18}$—; a group $R^{18}$— and a group —O—C(O)$R^{22}$.

17. A method according to claim 16, in which $R^{17}$ and $R^{17'}$ are a hydroxy group and a hydrogen atom, a $C_1$-$C_4$-alkyl group or a $C_2$-$C_4$-alkinyl group.

18. A method according to claim 17, in which $R^{17}$ and $R^{17'}$ are a hydroxy group and a hydrogen atom, a methyl, ethinyl or prop-1-inyl group.

19. A method according to claim 11, in which $R^{16'}$ stands for a group $R^{18}$—O— or $R^{19}SO_2$—O—.

20. A method according to claim 11, wherein the estratriene is

8β-vinyl-estra-1,3,5(10),9(11)-tetraene-3,17β-diol
3-methoxy-8β-vinyl-estra-1,3,5(10),9(11)-tetraen-17β-ol
8β-(2',2'-difluorovinyl)-estra-1,3,5(10),9(11)-tetraene-3,17β-diol
8β-(2',2'-difluorovinyl)-3-methoxy-estra-1,3,5(10),9(11)-tetraen-17β-ol
8β-vinyl-estra-1,3,5(10)-triene-3,17β-diol
3-methoxy-8β-vinyl-estra-1,3,5(10)-trien-17β-ol
8β-(2',2'-difluorovinyl)-estra-1,3,5(10)-triene-3,17β-diol
8β-(2',2'-difluorovinyl)-3-methoxy-estra-1,3,5(10)-trien-17β-ol
8β-vinyl-estradiol-3-sulfamate
8β-vinyl-estradiol-3,17-disulfamate
8β-vinyl-estradiol-3-(N-acetyl)-sulfamate
8β-vinyl-estrone-3-sulfamate
8β-vinyl-estron-3-acetate
8β-vinyl-estriol
8β-vinyl-estriol-3-sulfamate
8β-(prop-(Z)-enyl)-estradiol
8β-ethinyl-estradiol
17α-ethinyl-8β-vinyl-estra-1,3,5(10)-triene-3,17β-diol
17α-methyl-8β-vinyl-estra-1,3,5,(10)-triene-3,17β-diol
8β-vinyl-estra-1,3,5(10)-triene-3,17α-diol
8β-vinyl-estradiol-diacetate
8β-vinyl-estradiol-17-valerianate or
17β-acetoxy-8β-vinyl-estra-1,3,5(10)-trien-3-ol.

21. A method according for the treatment of hot flashes, sleep disturbances, irritability mood swings, incontinence, or vaginal atrophy comprising administering to a subject in need thereof an effective amount of an 8β-substituted estra-1,3,5(10)-triene compound of formula I'

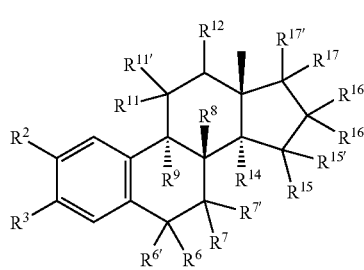

(I')

in which
$R^2$ means a hydrogen atom, a halogen atom;
a radical $R^{18}$ or $R^{18}$—O—, in which $R^{18}$ means a hydrogen atom or a straight-chain or branched-chain, saturated or unsaturated hydrocarbon radical with up to 6 carbon atoms or, a trifluoromethyl group;

a group $R^{19}SO_2$—O—, in which $R^{19}$ is an $R^{20}R^{21}N$, in which $R^{20}$ and $R^{21}$, independently of one another, mean a hydrogen atom, a $C_1$-$C_5$-alkyl radical, a group C(O)$R^{22}$, in which $R^{22}$ represents an optionally substituted, straight-chain or branched-chain, saturated or unsaturated in up to three places, an optionally partially or completely halogenated hydrocarbon radical with up to 10 carbon atoms, an optionally substituted $C_3$-$C_7$-cycloalkyl radical, an optionally substituted $C_4$-$C_{15}$-cycloalkylalkyl radical or an optionally substituted aryl, heteroaryl or aralkyl radical, or $R^{20}R^{21}N$ means a polymethylenimino radical with 4 to 6 C atoms or a morpholino radical;

$R^3$ means a group $R^{18'}$—O—, $R^{19}SO_2$—O— or —O—C(O)$R^{22}$, in which $R^{18'}$ is a hydrogen atom or a straight-chain or branched-chain, saturated or unsaturated hydrocarbon radical with up to 6 carbon atoms, a trifluoromethyl group, or an aryl, heteroaryl or aralkyl radical;

$R^6$ and $R^7$ each mean a hydrogen atom or together an additional bond;

$R^{6'}$ and $R^{7'}$, are each independently a hydrogen atom, a halogen atom, a group $R^{18}$—O—, $R^{19}SO_2$—O— or —$R^{22}$;

$R^8$ means a branched-chain, optionally partially or completely halogenated alkyl radical with up to 5 carbon atoms, or a straight chain or branched chain, optionally partially or completely halogenated alkenyl radical with up to 5 carbon atoms, an ethinyl or pro-1-inyl radical;

$R^9$ means a hydrogen atom, a straight-chain or branched-chain, saturated or unsaturated hydrocarbon radical with up to 5 carbon atoms, or together with $R^{11}$ means an additional bond;

$R^{11}$ means a hydrogen atom or together with $R^9$ or together with $R^{12}$ means an additional bond;

$R^{11'}$ means a hydrogen atom, a halogen atom, a saturated or unsaturated, optionally partially or completely halogenated (F, Cl) hydrocarbon radical, which has a maximum linear chain length of 4 carbon atoms, or group —X—$R^{18''}$, in which X is an oxygen or sulfur atom, and $R^{18''}$ is an alkyl radical with 1 to 3 carbon atoms;

$R^{12}$ means a hydrogen atom or together with $R^{11}$ means an additional bond;

$R^{14}$ means a hydrogen atom or together with $R^{15}$ means an additional bond;

$R^{15}$ means a hydrogen atom or together with $R^{14}$ or together with $R^{16}$ means an additional bond;

$R^{16}$ means a hydrogen atom or together with $R^{15}$ mean an additional bond;

$R^{15'}$ and $R^{16'}$, independently of one another, mean a hydrogen atom, a halogen atom, a group $R^{18}$—O—, $R^{19}SO_2$—O— or —$R^{22}$;

$R^{17}$ and $R^{17'}$ each mean a hydrogen atom; a hydrogen atom and a halogen atom; a hydrogen atom and an benzyloxy group; a hydrogen atom and a group $R^{19}SO_2O$—; a group $R^{18}$ and a group —C(O)$R^{22}$ or —O—C(O)$R^{22}$; a group $R^{18}$—O— and a group $R^{18}$—; a group $R^{18}$—O— and a group —O—C(O)$R^{22}$; or $R^{17}$ and $R^{17'}$ together a group =C$R^{23}$ $R^{24}$, in which $R^{23}$ and $R^{24}$, independently of one another, represent a hydrogen atom and a halogen atom, or together an oxygen atom, wherein said administration of the compound of formula I' achieves a selective effect on estrogen receptor beta.

22. A method according to claim 11, which is for the in-vitro treatment of male infertility.

23. A method according to claim 11, which is for the in-vivo treatment of male infertility.

24. A method according to claim 11, which is for the in-vitro treatment of female infertility.

25. A method according to claim 11, which is for the in-vivo treatment of female infertility.

26. A method according to claim 11, which is for the hormone replacement therapy in a patient in need of replacement of estrogen.

27. A method according to claim 11, which is for the therapy of osteoporosis.

28. A method according to claim 11, which is for the treatment of arteriosclerosis.

29. A method according to claim 11, which is for the treatment of benign prostate hyperplasia.

30. A compound having partial formula II or II'

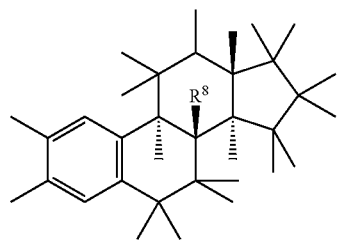

(II)

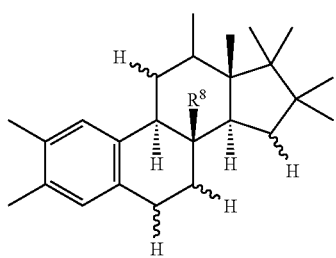

(II')

in which $R^8$ represents a straight-chain or branched-chain, optionally partially or completely halogenated alkyl or alkenyl radical with up to 5 carbon atoms, or an ethinyl- or prop-1-inyl radical, and in addition to the aromatic A-ring, one or more double bonds can be present in the B-, C- and/or D-ring in positions 6(7); 9(11); 11(12); 14(15) and 15(16), and substituents at carbon atoms 6, 7, 11, 15, 16 and 17 can be respectively in α- or β-position.

31. A method of achieving estrogenic action on bone, and not on uterine tissue, comprising administering a compound according to claim 30.

32. A pharmaceutical composition that contains at least one compound according to claims 1 and a pharmaceutically compatible vehicle.

33. A compound of formula I, according to claim 1, excluding compounds wherein $R^8$ is alkyl.

34. A method according to claim 21, wherein the treatment of hot flashes, sleep disturbances, irritability, mood swings, incontinence, or vaginal atrophy is in a subject undergoing hormone replacement therapy, and wherein said subject is in need of replacement of estrogen.

35. A method for
in-vitro treatment of male infertility;
in-vivo treatment of male infertility;
in-vitro treatment of female infertility;
in-vivo treatment of female infertility;
hormone replacement therapy in a patient in need of replacement of estrogen;
therapy of osteoporosis;
treatment of arteriosclerosis; or
treatment of benign prostate hyperplasia;
comprising administering to a subject in need thereof an effective amount of a pharmaceutical composition according to claim 32.

36. A method for the treatment of hot flashes, sleep disturbances, irritability, mood swings, incontinence, or vaginal atrophy comprising administering to a subject in need thereof an effective amount of a pharmaceutical composition according to claim 32.

37. A method according to claim 36, wherein the treatment of hot flashes, sleep disturbances, irritability, mood swings, incontinence, or vaginal atrophy is in a subject undergoing hormone replacement therapy, and wherein said subject is in need of replacement of estrogen.

38. A method according to claim 21, wherein mood swings are treated.

39. A method according to claim 21, wherein incontinence is treated.

40. A method according to claim 36, wherein mood swings are treated.

41. A method according to claim 36, wherein incontinence is treated.

* * * * *

UNITED STATES PATENT AND TRADEMARK OFFICE
CERTIFICATE OF CORRECTION

PATENT NO. : 7,378,404 B2  
APPLICATION NO. : 10/257288  
DATED : May 27, 2008  
INVENTOR(S) : Karl-Heinrich Fritzemeier It is certified that error appears in the above-identified patent and that said Letters Patent is hereby corrected as shown below:

Column 31, line 29 reads "togehter" should read --together--
Column 31, line 35 reads "hydrogne" should read --hydrogen--
Column 31, line 41 reads "togehter" should read --together--
Column 31, line 64 reads "groups" should read --group--
Column 31, line 66 reads "each mean hydrogen atom" should read --each mean a hydrogen atom--
Column 32, line 5 reads "optically" should read --optionally--
Column 32, line 21 reads "$R^{12}$, $R^{14}$, $R^{15}$" should read --$R^{12}$, $R^{14}$, $R^{15}$ and $R^{16}$--
Column 32, line 33 reads "halogenatom" should read --halogen atom--
Column 33, line 10 reads "—C(O)R" should read -- —C(O)$R^{22}$--
Column 34, line 54 reads "is a atom" should read --is a hydrogen atom--
Column 34, line 60 reads "$R^{6'}$ and $R^{7'}$, are each independently a hydrogen atom, a halogen atom," should read --$R^{6'}$ and $R^{7'}$ are each independently a hydrogen atom--
Column 34, line 67 reads "with up to 5 carbon atoms, an" should read --with up to 5 carbon atoms, an ethinyl or prop-1-inyl radical;--
Column 35, line 24 reads "$R^{17}$ and $R^{17'}$ each mean a hydrogen atom and a halogen atom" should read --$R^{17}$ and $R^{17'}$ each mean a hydrogen atom; a hydrogen atom and a halogen atom--
Column 36, line 8 reads "hydrogne" should read --hydrogen--
Column 36, line 29 reads "heteraryl" should read --heteroaryl--
Column 37, line 46 reads "irritability mood swings" should read --irritability, mood swings--
Column 38, line 64 reads "together a group" should read --together mean a group--

Signed and Sealed this

Second Day of September, 2008

JON W. DUDAS  
*Director of the United States Patent and Trademark Office*